US007573268B2

(12) United States Patent
Volegov et al.

(10) Patent No.: US 7,573,268 B2
(45) Date of Patent: Aug. 11, 2009

(54) DIRECT IMAGING OF NEURAL CURRENTS USING ULTRA-LOW FIELD MAGNETIC RESONANCE TECHNIQUES

(75) Inventors: Petr L. Volegov, Los Alamos, NM (US); Andrei N. Matlashov, Los Alamos, NM (US); John C. Mosher, Los Alamos, NM (US); Michelle A. Espy, Los Alamos, NM (US); Robert H. Kraus, Jr., Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/678,023

(22) Filed: Feb. 22, 2007

(65) Prior Publication Data

US 2007/0252595 A1 Nov. 1, 2007

Related U.S. Application Data

(60) Provisional application No. 60/775,905, filed on Feb. 22, 2006.

(51) Int. Cl.
*G01V 3/00* (2006.01)
(52) U.S. Cl. ........................... 324/309; 324/307
(58) Field of Classification Search ......... 324/300–322; 600/407–554; 128/653.1, 653.2, 653.3
See application file for complete search history.

(56) References Cited

U.S. PATENT DOCUMENTS

| 4,771,239 | A | * | 9/1988 | Hoenig | 324/248 |
|---|---|---|---|---|---|
| 5,254,950 | A | * | 10/1993 | Fan et al. | 324/322 |
| 5,265,611 | A | * | 11/1993 | Hoenig et al. | 600/409 |
| 5,339,811 | A | * | 8/1994 | Ohta et al. | 600/409 |
| 6,306,100 | B1 | * | 10/2001 | Prass | 600/554 |
| 6,833,701 | B2 | * | 12/2004 | Marek | 324/307 |
| 6,885,192 | B2 | * | 4/2005 | Clarke et al. | 324/300 |
| 6,996,261 | B2 | * | 2/2006 | deCharms | 382/131 |
| 7,187,169 | B2 | * | 3/2007 | Clarke et al. | 324/307 |
| 7,233,819 | B2 | * | 6/2007 | Eda et al. | 600/411 |
| 7,268,551 | B2 | * | 9/2007 | Lange | 324/318 |

(Continued)

OTHER PUBLICATIONS

Espy et al : IEEE transections on Applied Superconductivity, vol. 15, No. 2, pp. 635-639, Jun. 2005.*

(Continued)

*Primary Examiner*—Brij B Shrivastav
(74) *Attorney, Agent, or Firm*—Matthew F. Lambrinos; Kermit D. Lopez; Luis M. Ortiz

(57) ABSTRACT

Using resonant interactions to directly and tomographically image neural activity in the human brain using magnetic resonance imaging (MRI) techniques at ultra-low field (ULF), the present inventors have established an approach that is sensitive to magnetic field distributions local to the spin population in cortex at the Larmor frequency of the measurement field. Because the Larmor frequency can be readily manipulated (through varying $B_m$), one can also envision using ULF-DNI to image the frequency distribution of the local fields in cortex. Such information, taken together with simultaneous acquisition of MEG and ULF-NMR signals, enables non-invasive exploration of the correlation between local fields induced by neural activity in cortex and more 'distant' measures of brain activity such as MEG and EEG.

20 Claims, 13 Drawing Sheets

U.S. PATENT DOCUMENTS 7,372,274 B2 * 5/2008 Ardenkjaer-Larsen et al. .......... 324/321

OTHER PUBLICATIONS

Matlachov et al : Journal of Magnetic Resonance, vol. 170, pp. 1-7, 2004.*

McDermott et al: Science vol. 295, pp. 22472249, Mar. 22, 2002.*

Bodurka et al: Magnetic Resonance in Medicine, vol. 47, pp. 1052-1058, 2002. Xiong et al Human Brain Mapping, vol. 20, pp. 41-49, 2003.*

* cited by examiner

DIRECT IMAGING OF NEURAL CURRENTS USING ULTRA-LOW FIELD MAGNETIC RESONANCE TECHNIQUES

CROSS-REFERENCE TO RELATED APPLICATIONS

This application claims the benefit of U.S. Provisional Application No. 60/775,905 filed Feb. 22, 2006.

STATEMENT REGARDING FEDERAL RIGHTS

This invention was made with government support under U.S. Department of Energy Contract No. W-7405-ENG-36. Accordingly, the United States Government has certain rights in the invention.

TECHNICAL FIELD OF THE INVENTION

The present invention is generally related to the field of medical and biological imaging systems and methodologies. More particularly, the present invention is related to methods of imaging neurological currents in the brain and other biological currents in tissue. The present invention is also related to methods using ultra-low magnetic fields and highly sensitive magnetometers to measure biological currents including neural currents.

BACKGROUND

A variety of techniques have been developed to non-invasively image human brain function that are central to understanding how the brain works and to detect pathology. Current methods can be broadly divided into those that rely on hemodynamic responses as indicators of neural activity and methods that measure neural activity directly. The approaches all suffer from poor temporal resolution, poor spatial localization, or indirectly measuring neural activity.

The quest for higher spatial and temporal resolution brain imaging is driven by the evidence that knowledge of the structural-functional relationships within the human brain will greatly improve an understanding of brain function. Functional imaging studies provide information about cortical regions that form networks for attentional deployment, while electrophysiological studies have begun to unravel their millisecond-level temporal properties. High temporal resolution functional studies can elucidate oscillatory activity that is thought to structure the flow of information between distributed brain regions or be involved with information encoding and retrieval. Functional neuroimaging is also playing a growing role in human behavioral studies and the understanding of normal and abnormal function. Disease pathophysiology in epilepsy, for example, is dynamic in space and time and electrophysiological studies can provide clinically useful information for evaluating surgical potential in medically intractable partial epilepsy.

Functional magnetic resonance imaging (fMRI) is by far the most prevalent noninvasive functional brain imaging method in use today. Magnetic resonance imaging (MRI) spatially encodes the nuclear magnetic resonance (NMR) signature of nuclei, typically protons, in a volume of interest. The NMR signal arises from a population of spin-polarized nuclei precessing about a "measurement" field, $B_m$, with a characteristic "Larmor" frequency, $\omega_m = \gamma B_m$ (where $\gamma$ is the magnetogyric ratio). The NMR signal decays with time ('free induction decay' or FID) as transitions between spin states return the population to a Boltzman distribution (longitudal relaxation characterized by decay time $T_1$), and as spins in the population lose phase coherence (transverse relaxation characterized by $T_2$). The observed NMR decay time, $T_2^*$, is a combination of these and other effects such as spatiotemporal variations of $B_m$. Today's high-field (HF) MRI machines employ static magnetic fields in the 1.5 to >9 Tesla (T) range to yield exquisite anatomical resolution. The last decade has also witnessed an explosion in fMRI research and applications that detect hemodynamic (i.e. blood-flow and blood-oxygenation) changes that are thought to be related, albeit indirectly, to neural activity. Furthermore, while neural processes occur on a millisecond timescale, hemodynamic responses vary on the timescale of seconds. Thus, even as fMRI can provide exquisite spatial resolution, it is only an indirect (at best) measure of neural activity with sluggish temporal resolution.

In contrast, magnetoencephalography (MEG) and electroencephalography (EEG) noninvasively measure the magnetic and electric fields generated directly by neural activity. While these modalities yield detailed temporal information (milliseconds or better), the spatial localization must be inferred from spatial modeling priors resulting in the classic ill posed inverse problem of electromagnetism. Thus, while MEG and EEG provide superb temporal resolution, the electrophysiological "imaging" is only "indirect" at best.

Researchers have recently proposed that neuroelectrical activity may interact with a spin-polarized population to cause a measurable phase change in the population, that may enable "direct neural imaging" (DNI) using MRI methods. Several studies have focused on the feasibility of DNI at HF (High Frequency), including those using current phantoms (passing a current through a bolus of water). These studies concluded, based on both modeling and experimental results, that DNI at HF may be possible. While most phantom studies used currents orders of magnitude larger than produced in the brain, one study investigated sources with current dipole equivalent amplitudes of ~10-100 nA-m, approximately representative of human evoked brain activity. A common problem with all of these studies was the use of effective DC currents while human brain activity is more accurately characterized by waveforms that contain a broad distribution of frequencies with roughly "zero-mean" amplitude over typical MR measurement time windows. Such a time-varying current distribution would have a far smaller effect on the NMR signal than a DC current. In the limiting case of a correlated zero-mean current distribution, the phase effects would integrate to zero resulting in no detectable current-induced difference in the NMR signal. Furthermore, the phantom studies avoided susceptibility artifacts that would otherwise be a significant confound at HF.

The only in vivo experimental measurement of DNI at HF has been vigorously debated in the neuroimaging community. A serious confound for this, or any HF measurement, is the "susceptibility artifact" caused by the different magnetic properties of oxy- and de-oxy hemoglobin—an effect that is orders of magnitude larger than the expected direct neural effect on the NMR signal. Indeed, these susceptibility differences are the basis for fMRI and because they accompany neural activity, they become the greatest impediment to measuring DNI at HF. Furthermore, because human brain activity does not produce DC currents, the expected phase effects would be far smaller than phantom experiments performed to date would lead one to believe.

What is needed is a physical system and new techniques to tomographically image the direct consequences of neural activity. It has been suggested that the NMR phase will be altered by neural activity and imaged by MRI methods. While demonstrating this effect has been elusive, the present inventors now describe how ultra-low field MRI is more sensitive for measuring neural activity. Resonant mechanisms at ultra-low fields can further enhance the effect of neural activity on NMR signals. The observed resonant interactions described in detail herein can form the foundation of a new functional neuroimaging modality capable of high resolution direct neural activity and brain anatomy tomography.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The aforementioned aspects of the invention and other objectives and advantages can now be achieved as described herein.

It is a feature of the present invention to provide methods for noninvasively and directly imaging neural activity using Nuclear Magnetic Resonance (NMR) techniques at Ultra Low Frequencies (ULF).

It is another feature of the present invention to provide a system for noninvasively and directly imaging neural activity using Nuclear Magnetic Resonance (NMR) techniques at Ultra Low Frequencies (ULF).

It is yet another feature of the present invention to provide a system for noninvasively and directly imaging neural activity using Nuclear Magnetic Resonance (NMR) techniques at Ultra Low Frequencies (ULF) using SQUID sensors.

It is yet another feature of the present invention to provide a method for simultaneously imaging anatomy, neuronal activity and MEG using the same sensor system array (e.g., SQUID sensor array).

It is also a feature of the present invention to provide a system to provide imaging in accordance with the methods described herein, the system including a single SQUID sensor adapted for operating at measurement fields of 2-25 uT and is further adapted with a pre-polarizing field from 4-30 uT generated by at least one room-temperature, wire-wound coil that is turned off during measurement operations. The system can have geometry with samples located outside of a cryostat at room temperature, removing constraints on sample size and enabling the capture of signals from living tissue.

The present inventors have found that neuronal currents (both intra- and extra-cellular) will interact with the proton spins in tissue resulting in a measurable change in the NMR signal that can be localized using ULF MRI techniques. The present inventors have enabled development of new models demonstrating an entirely new signature of neural (and any bioelectric) activity that can be tomographically imaged. The inventors demonstrate that nuclear magnetic resonance (NMR) techniques at ultra-low fields (<100 microtesla) can be used to unambiguously detect and ultimately directly image neural activity. NMR at ULF provides several benefits, based on the basic properties of the process, which are not realized at high fields.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
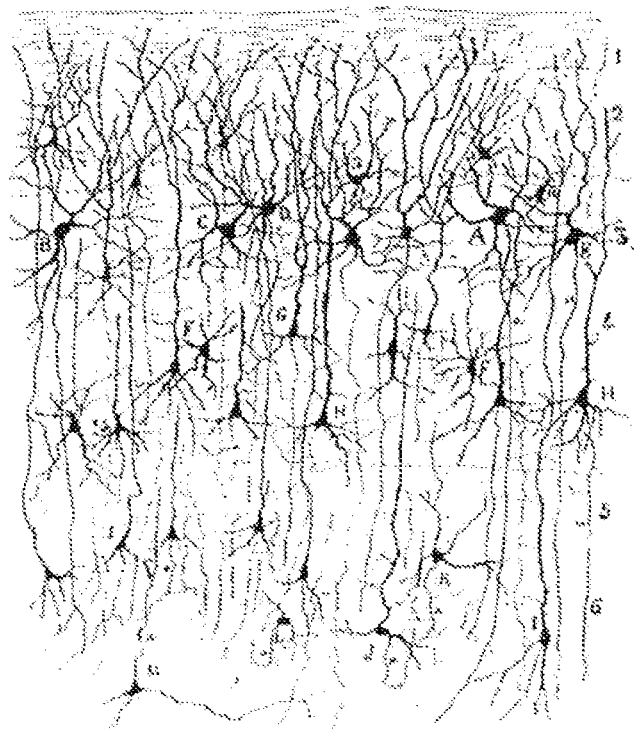
FIG. 1 illustrates the complex spatial organization of neurons in cortex.

Electric currents associated with neuronal activity generate magnetic fields that affect the precession of the spins in cortical tissue. This effect can be used to detect (and image) neuronal activity. The currents result from a large number of fast microscopic ion transport processes such as postsynaptic currents and action potential currents from many individual neurons comprising cortical tissue. FIG. 1 illustrates the complex spatial organization of neurons in cortex. The average duration of a composite postsynaptic potential is on the order of 10 ms; the average duration of an action potential is on the order of 1 ms. From a distance, postsynaptic currents appear to be a current dipole with average strength of roughly 20 fA-m per neuron. In contrast, currents associated with action potentials can be approximated by two oppositely oriented current dipoles with a separation of about 1 mm and magnitude of each dipole about 100 fA-m. Since the two dipoles are in opposite directions, they form a current quadrupole.

For a cortical area of several square millimeters, magnetic fields produced by each individual neuron observed at a distance of a few centimeters are almost the same due to the parallel alignment of neurons typical of cortex. Thus the fields associated with a population of neurons sum to produce a field on the order of 10-12 T for spontaneous activity and 10-13 T for evoked responses. These are the fields typically measured by MEG.

Figure 2:
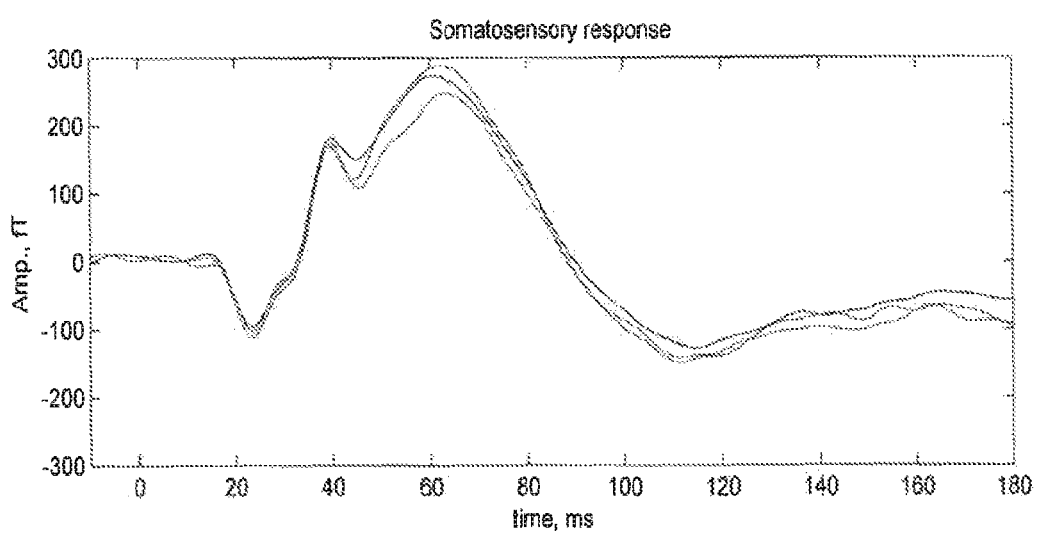
FIG. 2 illustrates a typical somatosensory response recorded with the LANL SIS MEG system.

Since a dipolar field produced by postsynaptic current, decreases with distance as $1/r2$, and the quadrupolar field resulting from action potentials falls off as $1/r3$, the field measured at a few centimeters distance will be dominated by synchronized activity of postsynaptic currents. It is commonly assumed that at least 50,000 or more cortical neurons must coherently act to produce the magnetic fields detectable by MEG. Because the fields from a large number of neurons are superposed to produce the resulting measured field, the frequency content in the resulting signal is typically less than 100 Hz. FIG. 2 illustrates a typical somatosensory response recorded with the SIS MEG system at Los Alamos National Laboratory by the inventors.

To understand the effect of neuronal currents on the NMR signal for a given area of cortex, one must consider the field generated by neurons inside cortical tissue. At the microscopic level the picture is quite different. First, because the separation between the source (neuronal current) and the 'observer' (the nuclear spins being affected) is very small, currents associated with action potentials can no longer be considered negligible and must be taken into account, together with the postsynaptic currents. Second, the current dipole model for postsynaptic and action potential currents are no longer valid and should be augmented.

Based on the general spatial organization of current sources in cortical tissue, the following plausible statements can be made about the magnetic fields inside the tissue. The magnetic field pattern generated by neuronal currents will be non-uniform over the microscopic spatial scale of the neurons as a consequence of the cortical tissue structure. Thus the precessing spins that underlie the NMR signal should locally exhibit varying spread of frequencies, resulting in local variations in the T2 relaxation time that will depend on the microscopic neuronal current density distribution. This general mechanism does not induce transition between energy levels and does not change population of energy levels. In addition, because the magnetic field generated by neuronal currents at some arbitrary point inside tissue is largely the consequence of a relatively small number of neighboring neurons, and the fields generated by these neurons have random relative orientation to a point inside the tissue, one can appreciate that the field will have an oscillatory character with frequency content up to ~1 kHz.

Figure 3:
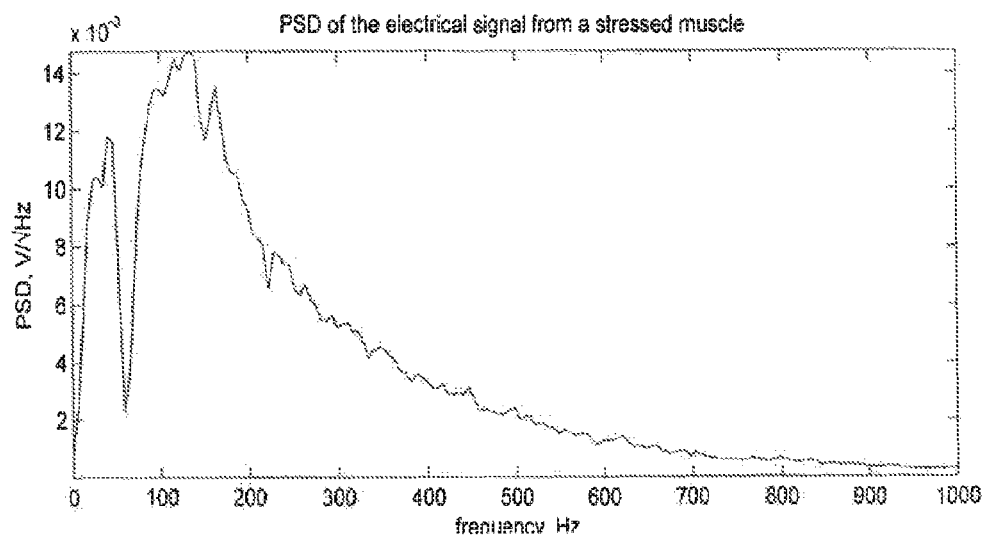
FIG. 3 illustrates a practical example that has some relevance to the issue at hand, the power spectrum of electromyography signal of a stressed muscle.

A practical example that has some relevance to the issue at hand, the power spectrum of electromyography signal of a stressed muscle, is illustrated in FIG. 3. FIG. 3 clearly shows a power spectrum density extending up to several hundred Hz. Simple model calculations further confirm that point. Also, there have been other studies of frequency content of biomagnetic activity, including some evidence of higher frequencies (~600 Hz) in brain activity, even at large 'observer' distances.

The effect of these oscillating fields on an NMR signal can be considered in terms of NMR relaxation mechanisms which require two conditions: 1) there must be an interaction that operates directly on spins; 2) the interaction must be time dependent. Time-varying magnetic fields represent one such interaction. The time dependence of the interacting field must be on a suitable time scale. If the magnetic field variation is much faster (higher frequency) or much slower (lower frequency) than that of the NMR resonance (Larmor) frequency, then little effect will be observed on the NMR signal compared to the absence of the interacting field. However, when the variation of the interacting field is at or closely matches the NMR Larmor frequency, then the interacting field will interact significantly with the spin population responsible for the NMR signal through the process called resonant absorption.

Local biological currents and the corresponding magnetic fields, as discussed above, vary with frequencies typically below a few kHz. When NMR signatures are measured at ULF (below 100 uT), the Larmor frequency for protons will be below 4 kHz. These conditions are precisely those required to satisfy the conditions for interaction between the biomagnetic fields and the NMR spin precession through resonant absorption. In fact such interactions can induce transitions between energy levels, thus changing T1 relaxation time. Thus, one can use this relaxation mechanism for tomographic imaging of bioelectric activity in a fashion that could not be realized at higher fields (because of the mismatch between biomagnetic and Larmor frequencies). For this reason, ULF-NMR, together with the strengths of ULF-MRI mentioned above, has been discovered by the present inventors as being uniquely suited to measure, and ultimately image neuronal current activity.

The present inventors' work in ULF-NMR and MRI have demonstrated a variety of approaches to reconstructing images from NMR measurements, in particular those obtained with superconducting quantum interference device (SQUID) sensors. The inventors have also demonstrated that the same SQUID sensors can simultaneously collect neural activity (MEG) and NMR data.

Demonstrating the feasibility of DNI using NMR techniques at ULF leads to a new and powerful neuroimaging tool that can simultaneously image anatomy (by ULF-MRI), neuronal activity (by DNI), and MEG using the same SQUID sensor array. Simultaneous acquisition of anatomy and DNI removes errors inherent in coregistration of data acquired by different systems, enabling direct correlation of function and anatomy. DNI, while a direct tomographic measure of neuronal activity, may be limited in temporal resolution to 10-100 ms. Simultaneous acquisition of the MEG component can therefore enable temporal interpolation between the DNI measurements with millisecond resolution while providing strong constraints for the MEG inverse based on the same direct neuronal activity that leads to the MEG measurement.

The present inventors have experimentally demonstrated ULF-MRI, using fields $10^4$-$10^6$ times weaker than HF-MRI. While the NMR signals are dramatically weaker at ULF than HF, the inventors used SQUID technology to generate MRI images. The inventors also demonstrated the first simultaneous measurement of MEG and NMR signals, laying the foundation for simultaneous MEG (brain function) and ULF-MRI (anatomy).

The present inventors have found that typical $B_m$ for ULF-NMR and MRI work is in the 1-100 microtesla ($\mu$T) range with corresponding proton $\omega_m$=40~4000 Hz. They also noted that the power spectra for neural activity extends to a few kHz range. The exact shape of the neural activity spectrum depends strongly on the stimulus causing the cortical activation; however the peak typically occurs below 100 Hz with little energy above about 2 kHz. Recognizing the overlap between proton Larmor frequency at ULF and the neural activity spectrum leads to the hypothesis that interactions between the spin population and neural activity in cortex can be dominated by resonant mechanisms that are unique to ULF. Demonstrating this mechanism provides the foundation for the new functional neuroimaging modality presented herein: ultra-low field direct neural imaging (ULF-DNI).

Figure 4:
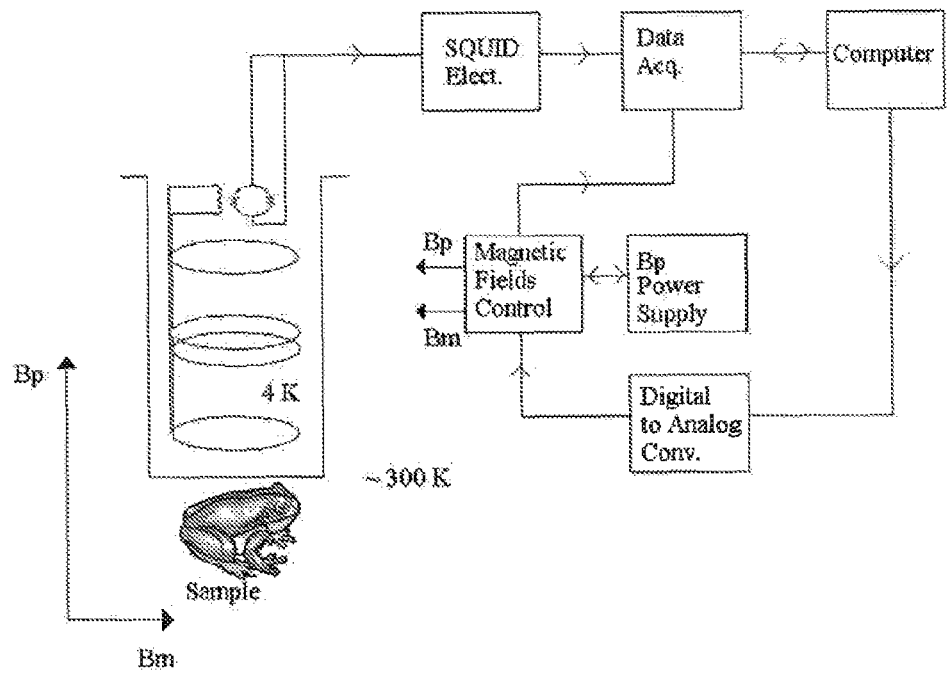
FIG. 4 illustrates a diagram for a system similar to that used by the inventors in obtaining neural current measurements.

The present inventors have built and demonstrated a prototype NMR system that employs a single SQUID sensor and has been used with measurement fields of 2-25 $\mu$T. Referring to FIG. 4, a diagram for a system similar to that used by the inventors is illustrated. The system used a pre-polarizing field from 4-30 mT generated by simple room-temperature wire-wound coils that are turned off during measurements. The instrument has an open geometry with samples located outside of the cryostat at room temperature (clearly a necessary prerequisite for human studies), removing constraints on sample size and allowed the acquisition of signals from living tissue. The inventors obtained 1H NMR spectra from a variety of samples, and also acquired gradient-encoded free induction decay (FID) data from a water-plastic phantom in the $\mu$T regime from which projection images were reconstructed. NMR signals from samples inside metallic containers have also been acquired. This is possible because the penetration skin depth is much greater at the low NMR frequencies of this system than for conventional systems. This achievement demonstrates that even subjects with significant metallic implants could be imaged at ULF. Advantages to ULF-NMR measurements include lower susceptibility artifacts caused by high fields, negligible line width broadening due to measurement field inhomogeneity, and reducing the burden of producing highly homogeneous fields.

Referring again to FIG. 4, the system used a low-Tc SQUID 115 coupled to a superconducting second-order axial gradiometer as the detector. Schematic diagram of the system illustrating that it was developed for room-temperature $\mu$T NMR. The inventors used a fiberglass liquid helium cryostat with a low-Tc SQUID with 2 $\mu\phi 0/\sqrt{Hz}$ noise connected to an axial superconducting second-order gradiometer (14 mm diameter, 50 mm baseline). Bp is provided by two 250-turn, 80 mm diameter coils, separated by 60 mm. The coils were positioned around the tail of the cryostat as indicated by reference numeral coaxial to the gradiometer and adjusted to minimize pick-up. A square Helmholtz coil of length 56 cm provides the measurement field, Bm, orthogonal to Bp. Additional components that made up the test system included SQUID electronics module, data acquisition module, magnetic fields control module, Bp power supply, computer and a digital-to-analog converter operational between the digital computer and the analog magnetic field control module.

The detection system as shown is a typical design that can be used in biomagnetic measurements in accordance with carrying out the teachings of the present invention. The sample in FIG. 4 is illustrated as a frog. The sample was pre-polarized in a magnetic field, Bp of 4-30 mT, while the measurement field, Bm, was ~3 orders of magnitude lower, between 2-25 $\mu$T. Operation at below the Earth's magnetic field was achieved by using a passive magnetic shielding and by adjusting the measurement field to offset residual environmental fields. The passive shielding also reduced the ambient magnetic noise detected by the SQUID sensors. Bp was generated by two coils positioned coaxially to the gradiometer and positioned such that the superposition of the fields from the two coils minimized the pre-polarization field coupling to the gradiometer. Bm was generated orthogonal to Bp by a square Helmholtz coil set. Gradient fields, when required, were generated in this early system along the Bm direction by unbalancing the Helmholtz coils. It should be noted that the inventors also were able to obtain free induction decays (FIDs) with the pre-polarizing field oriented perpendicular to both the gradiometer's axis and measurement field.

Samples were pre-polarized in Bp for a time greater than T1 while the SQUID electronics were effectively turned off. The much smaller measurement field, Bm, was present continuously. At time t=0, Bp was switched off in 0.5 msec, after which the SQUID electronics were activated, and the precession signal about Bm was measured. A dead time associated with SQUID recovery and dewar magnetization was observed to be ~2 msec; small compared to T1 and T2 times for the samples. The spin precession signals were directly digitized (frequency range 100-1000 Hz) making heterodyne detection unnecessary. The signal-to-noise ratio (SNR) measured for a water sample at 10 mT Bp and 10 $\mu$T Bm was ~1 in a 100 Hz bandwidth and was enhanced through averaging. Another important strategy for SNR improvement is through the use of higher Bp fields. An enhancement factor of 10-20 should be straightforward for many applications.

Free induction decay signals and spectra for the 1H signal were obtained from a number of samples at $\omega$L from 90 to 1000 Hz. The inventors consistently observed a difference in the apparent T1 relaxation rate as a function of the magnitude of Bm. While a systematic investigation of the T1 dependence on Bm must be completed, similar observations have been reported suggesting the possibility of T1 contrast imaging. Similar FID measurements for mineral oil have been presented; however the sample in that early work was confined inside the cryostat and actively heated for those measurements. As depicted in FIG. 4, samples have been in the open, outside the cryostat more than 1 cm from the sensor coils.

Figure 5:
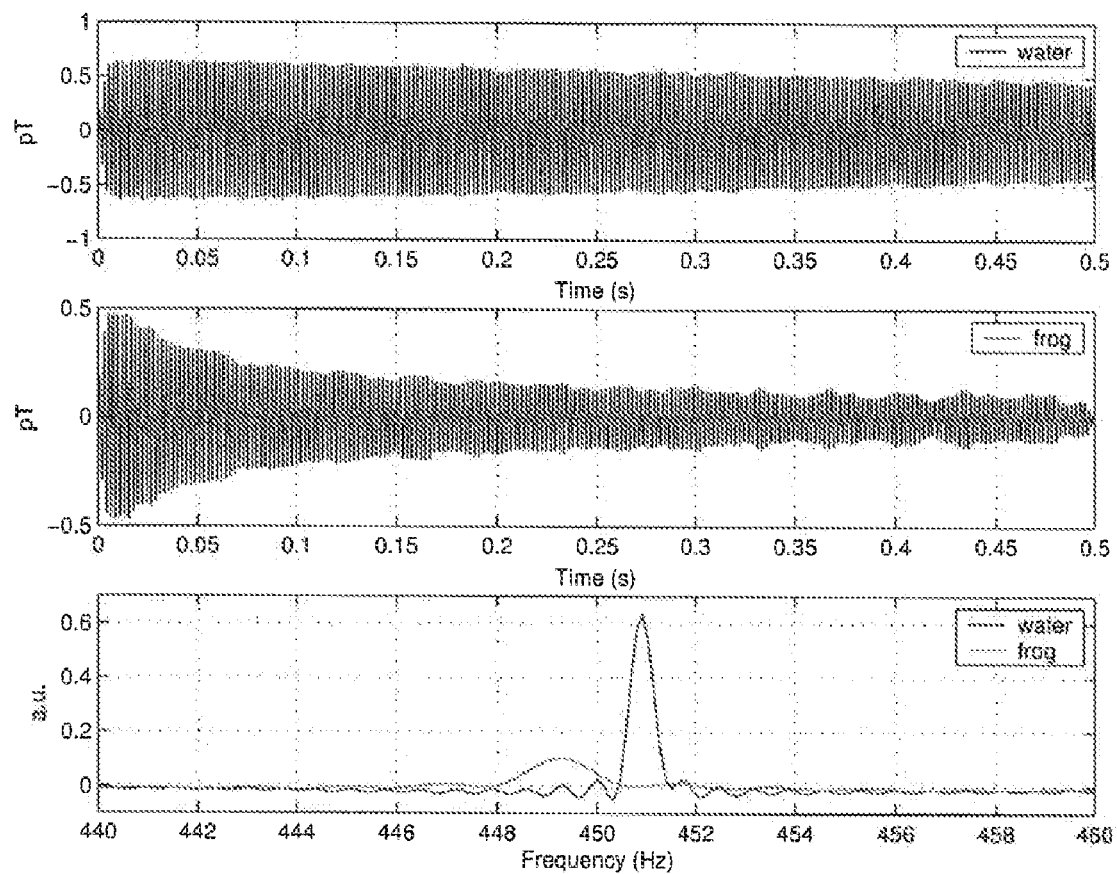
FIG. 5 illustrates the FIDs and spectra for the 1H signal from water and a live frog.

FIG. 5 illustrates the FIDs and spectra for the 1H signal from water and a live frog, which is the sample shown in FIG. 4. Top, Center) FIDs for 1H signal from water phantom and a live frog (Bottom) 1H spectra from water and a live frog with $Bp\approx20$ mT and $Bm\approx10$ µT. Plots represent averages over 100 epochs. To the inventors knowledge the only other NMR signals detected and imaged from living samples by a SQUID system were at 10 mT magnetic fields. The data taken on the frog employed a measurement field approximately 3 orders of magnitude lower at 10.5 µT. While data was epochaveraged, signals were visible in a 10 Hz bandwidth (SNR>1) even for single epochs.

Figure 6A:
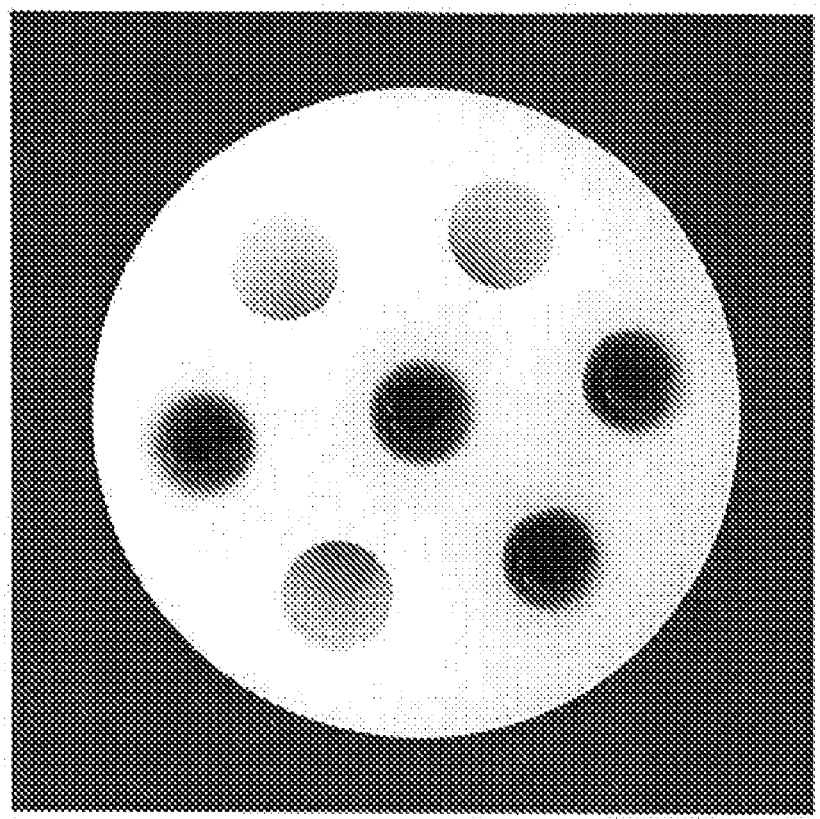
FIG. 6(a) is a reproduction of a photograph of a 60 mm diameter by 52 mm high cylindrical plastic phantom with seven 10 mm diameter by 48 mm deep wells.
Figure 6B:
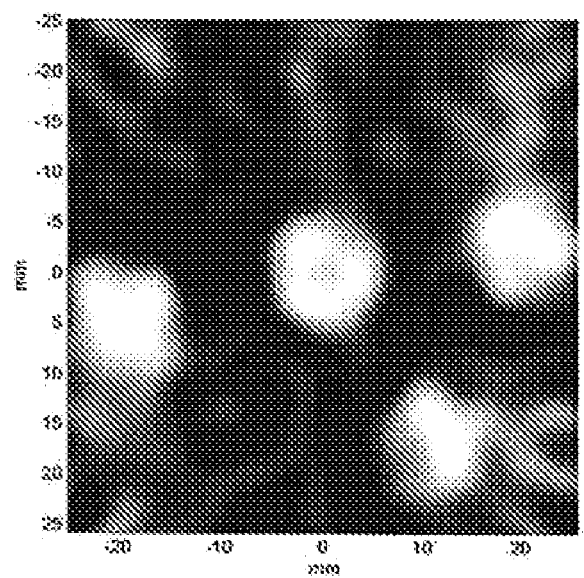
FIG. 6(b) is a reproduction of a 2D image of the phantom constructed from a series of gradient encoded FID spectra acquired at various angles by rotating the sample within a fixed measurement field.

FIG. 6(a) is a photograph of a 60 mm diameter by 52 mm high cylindrical plastic phantom with seven 10 mm diameter by 48 mm deep wells. Four of the wells were filled with water (shown filled with colored water for visibility). FIG. 6(b) illustrates a 2D image of the phantom constructed from a series of gradient encoded FID spectra acquired at various angles by rotating the sample within a fixed measurement field. The measurement field was 7.8 µT and the gradient was ~7 µT/m. Given the small Bm field, it can be noted that the field orientation could be readily rotated to arbitrary directions using a fixed set of field coils and appropriately phasing the relative current amplitudes rather than rotating the sample.

Spatial encoding of these FIDs across the volume of interest is achieved by applying and switching gradients of the magnetic field. In creating this image, the inventors identified many issues and advantages of ULF-MRI that are not present at HF. Simply using HF imaging techniques at ULF will generally result in poor image quality, but ULF represents imaging opportunities unavailable at HF.

Figure 7:
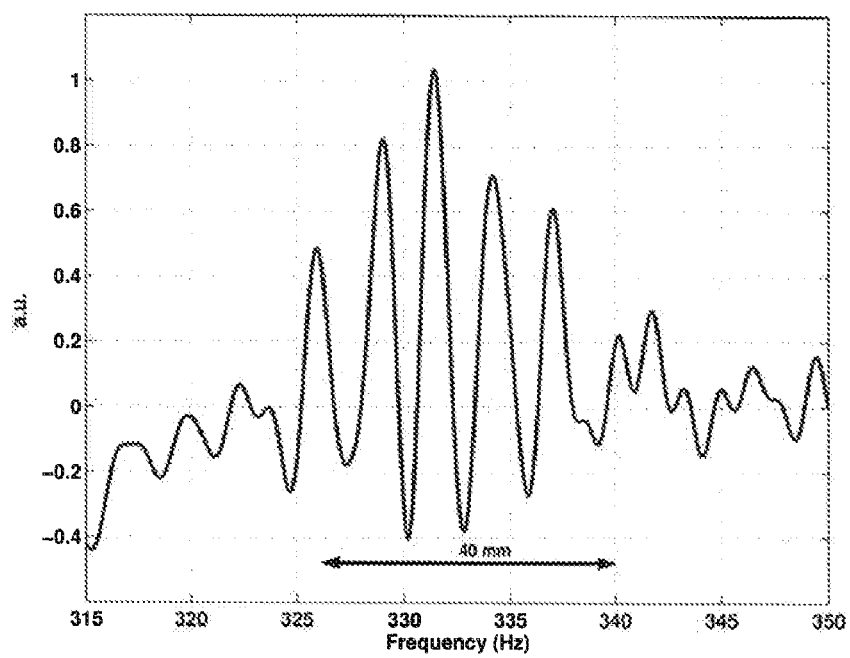
FIG. 7 illustrates a one-dimensional gradient encoded frequency spectrum obtained from a simple waterplastic phantom.

Referring to FIG. 7, illustrated is a one-dimensional gradient encoded frequency spectrum obtained from a simple waterplastic phantom. The phantom consisted of a plastic cylinder with six 4 mm diameter wells arranged in a row along the diameter (center to center distance 8 mm). All six filled holes are clearly resolved. The change in amplitude for the peaks representing the wells reflects a positional sensitivity that agrees well with simulations. For these measurements Bm=7.8 µT and the gradient was 8 µT/m. FWHM analysis of these data confirms a spatial resolution of approximately 1 mm.

A principal objective of the inventors during experimentation was to demonstrate the feasibility of NMR and MRI at ULF, a regime that ultimately may have numerous applications. One such application is simultaneous MRI and MEG measurements, two techniques previously considered incompatible. Simultaneous MEG and ULF-MRI may alleviate some of the difficulties imposed by the current need to co-register separately acquired MEG and high-field MRI data. The inventors achieved simultaneous ULF-NMR and MEG. Simultaneous MRI and MEG will require imaging at the lowest fields possible to minimize interference with MEG signal acquisition. Imaging at fields of 1-10 mT has previously been demonstrated and has been reported at 130 µT. To the inventors' knowledge, the results obtained were the first MR images in the 10 µT regime with a sample outside of the cryostat.

By working at ULF, the inventors achieved narrow line widths that approach the natural line width. The narrow line widths of ULF measurements may allow improving imaging resolution without a corresponding increase in gradient strength. Finally, because T1 roughly equals T2 for most liquid samples at ULF, the delay between successive acquisitions may be reduced to less than 100 msec, increasing the SNR per unit measuring time. Because Bm orientation is arbitrary (it is not fixed by the large static field of the imaging magnet), gradient design is simplified, i.e., all gradients can employ designs analogous to the z-axis gradient of a conventional imager. The flexibility of choosing Bp and Bm orientations may enable the design of gradient fields with a minimum of parasitic gradients (see discussion in the following section). Gradient distortions can be reduced by the smaller gradient requirements for imaging. Imaging dynamic physiological processes and in particular functional imaging of neural activity drives a requirement for much faster imaging.

While MR imaging at ULF has many advantages, a variety of new challenges arise. The speed at which signals necessary for image reconstruction can be acquired at ULF is limited by the natural line width and the minimum Nyquist sampling rate. While the dwell time is inextricably coupled to $\omega_L$, images are reconstructed from a large number of measurements. A number of labs have explored the use of phased arrays for detection coupled with novel image reconstruction techniques. The inventors investigated applying dense-array SQUID sensor system designed for MEG applications to study various new approaches to increase MR imaging speed at ULF. MR/MRI at low fields introduces a host of new applications including true ex situ imaging, "pure J spectroscopy", and low-cost MR instrumentation. With the reduction in susceptibility noise and enhanced resolution at low fields, it is now possible to conduct simultaneous NMR/MRI and MEG or other biomagnetic measurements.

The inventors' work has demonstrated basic proton spectroscopy at microtesla fields, and extended the measurements to simple imaging with samples located outside of the cryostat, demonstrating that there are no fundamental limitations to prevent anatomical or functional imaging of a human subject. NMR inside metal containers has also been demonstrated, something that could not be accomplished with conventional high-field methods.

Figure 8A:
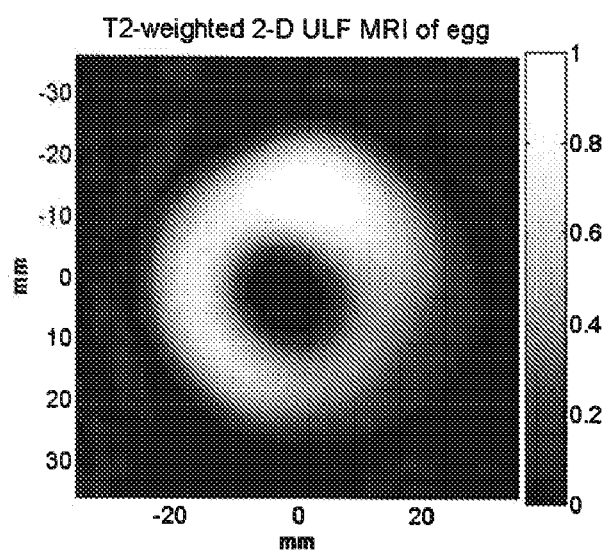
FIG. 8 illustrates a 2-D ULF T2*-weighted image of a chicken egg (larger image)
Figure 8B:
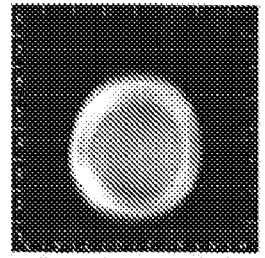

Finally, the inventors present here the first T2*-weighted image acquired at ultra-low field. FIG. 8(a) shows a 2-D ULF T2*-weighted image of a chicken egg (larger image). The inventors used a measurement field, Bm=12 µT, and a pre-polarizing field, Bp=25 mT. A gradient, G=28 µT/m was used for frequency encoding. A high-field (1.5 T) image of a chicken egg is shown in FIG. 8(b) inset below the ULF image.

Figure 9:
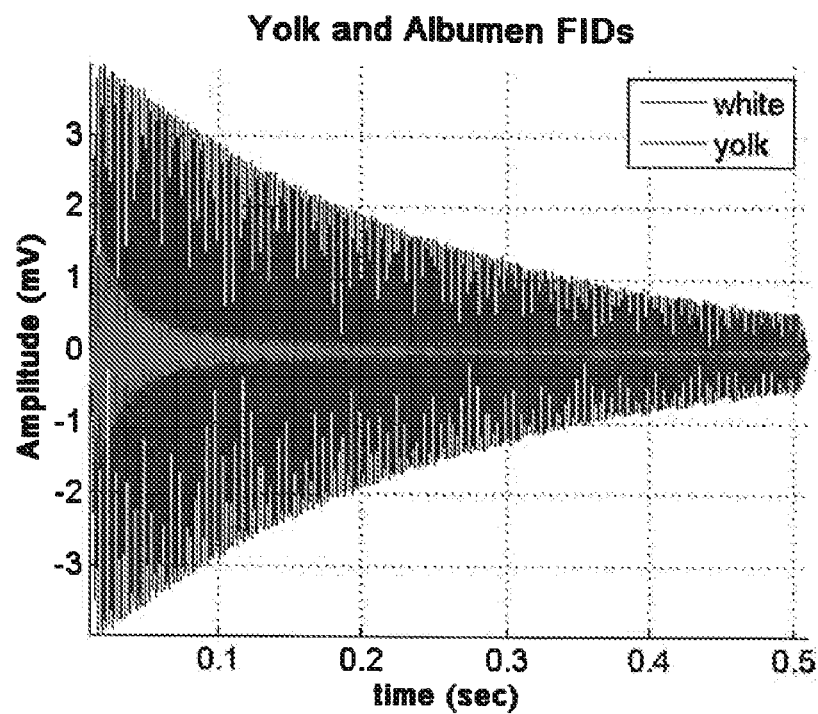
FIG. 9 illustrates raw FID data for both components of the chicken egg (yolk and albumen)

The inventors show raw FID data for both components of the chicken egg (yolk and albumen) in FIG. 9 acquired at ULF (Bm=12 µT and Bp=25 mT). The measured T2* values were: T2*(albumen)=240 msec and T2*(yolk)=36 msec. This is an extremely important milestone for anatomical imaging as it is anticipated that T1 and T2 weighted images are likely to yield higher contrast than density for the human brain structure.

Figure 10:
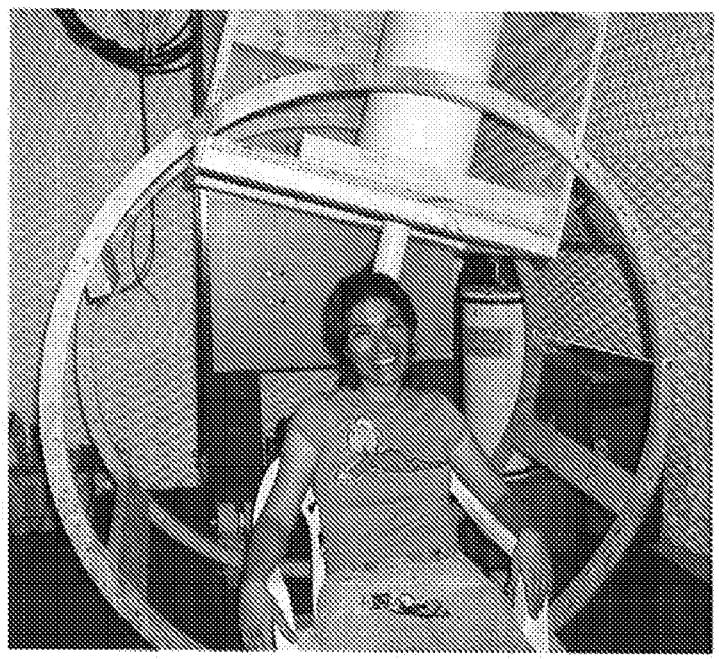
FIG. 10 illustrates a photograph reproduction of a simple prototype system capable of simultaneously measuring MEG and NMR signals from the human brain.

The inventors demonstrate in this section the ability to acquire direct measurements of functional neuromagnetic data (MEG) simultaneously with ULF-NMR signals using SQUID sensors. Referring to FIG. 10, a simple prototype system capable of simultaneously measuring MEG and NMR signals from the human brain was constructed. A SQUID sensor coupled to a gradiometer pickup coil is used to simultaneously measure these signals. 1H NMR spectra with typical $\omega_L$=100-1000 Hz were acquired simultaneously with the evoked MEG response from a stimulus to the median nerve. The single SQUID sensor was placed approximately over the somatosensory cortex of a normal human subject to noninvasively record the signals.

Figure 11:
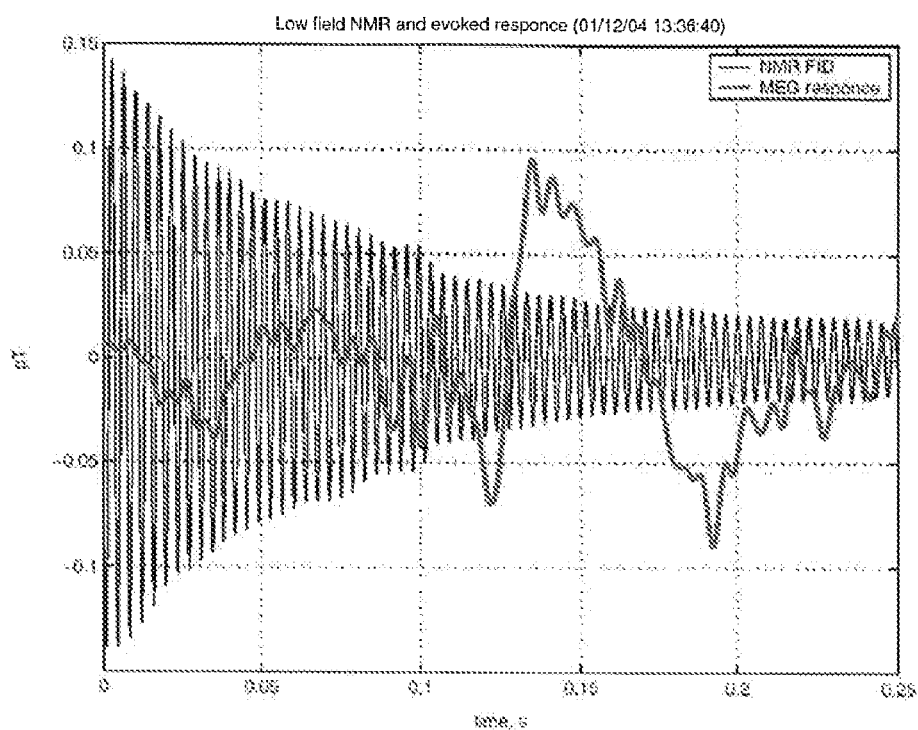
FIG. 11 illustrates a graph of both a 1H NMR FID (blue trace) and MEG somatosensory response (red trace) acquired from a region of the human head including the somatosensory cortex.

Referring to FIG. 11, a graph shows 1H NMR FID (blue trace) and MEG somatosensory response (red trace) acquired from a region of the human head including the somatosensory cortex. The complex FID is consistent with a multiple T2* components.

These measurements demonstrated acquisition of signals necessary for simultaneous MRI and MEG. NMR in the microtesla regime provides narrow line widths and the potential for high spatial resolution imaging while SQUID sensors enable direct measurement of neuronal activity with high temporal resolution via MEG.

Recording NMR signals in low fields (B<10-5 T) opens up the possibility of acquiring tomographic anatomical images simultaneously with high-temporal resolution measurements of MEG, as the magnetic fields required for imaging are now compatible with SQUID sensors. The inventors obtained the NMR signal by pre-polarizing the sample in a ~5 mT magnetic field, Bp, while the measurement field, Bm, was ~3 orders of magnitude lower at 6.3 µT. As in the previous section, the inventors used a low-Tc SQUID coupled to a first-order tangential (planar) gradiometer here. The pre-polarizing field, Bp, is produced by a 64 mm diameter coil with 230 turns positioned co-axial to the tail of the cryostat. A 56 cm square Helmholtz-style coil provides the measurement field, Bm, orthogonal to Bp. The orientation of the planar gradiometer is orthogonal to both Bm and Bp coils to minimize flux coupled into the SQUID. The tail of the cryostat containing the gradiometer was placed directly over the somatosensory cortex region of the human subject, minimizing standoff, which in the inventors' case was about 12 mm. The whole system is placed inside a single layer magnetically shielded room (MSR). The shielding factor of the MSR is about 40 at 1 Hz and about 200 at 60 Hz, and the residual DC magnetic field is below 0.1 µT. The somatosensory evoked response was produced by applying an electrical current to the median nerve by an isolated Grass stimulator using two electrodes attached to the forearm just above the wrist. The typical measurement protocol consisted of the pre-polarization of the cortex area for 1.5 sec, a time that is comparable with the expected T1 (about 0.95 sec for gray matter, 0.6 sec for white matter). While Bp is applied the SQUID is effectively turned off. The measurement field Bm is always on. At time t=0, Bp was slewed to zero in less than 0.5 msec, and after a variable delay (0-100 msec), the stimulus is presented. The SQUID electronics are activated at t=10 msec and signal acquisition begins at t=15 msec.

The first-order gradiometer coupled to a SQUID reduces uniform ambient magnetic fields by more than 80 dB while remaining extremely sensitive to fields emanating from nearby sources (such as the subject head). The total white noise of the system recalculated to the lower pick-up coil is approximately 8 fT/$\sqrt{Hz}$, most of which is caused by noise from the cryostat. The inventors' practical signal-to-noise ratio (both for NMR and MEG signals) is about 1 in a 100 Hz bandwidth. Data epochs for approximately 200 presentations of the stimulus were averaged after removing specific noise components (power line harmonics, cryostat demagnetization signal, and eddy current signal). The FID and MEG signals were separated by applying a 150-450 Hz bandpass filter and a 3-100 Hz bandpass filter to the averaged data, respectively.

Referring to FIG. 11, illustrated graphically is the separated 1H FID signal (blue line) and MEG somatosensory response (red line) from a human brain. The NMR and MEG data were measured simultaneously with the same SQUID sensor. The stimulus was presented at t=100 msec (producing the artifact seen in the FID), and the expected N20 response at 20 msec post-stimulus and subsequent somatosensory components are clearly visible. While both FID and MEG signals are clearly visible, the inventors' system configuration relative to the subject resulted in a diminished signal amplitude (factor of ~3) from what the inventors obtained at the optimal gradiometer position. MEG data obtained without simultaneous NMR measurements (Bp=0, not shown) produced signals of the same shape and amplitude.

The shape of the FID curve implies the presence of multiple frequency components. To resolve the FID the inventors used the DECRA algorithm. The primary component in the 1H FID signal for the subject head that accounted for more then 80% of the signal strength is characterized by f0=268.5 Hz, and T2*=86 msec. The origin of the remaining components is still under investigation; however, it is likely due to the variation of T2* for different tissue types in the brain. If this hypothesis is proven, this would serve as an excellent contrast mechanism for anatomical imaging of the brain. An estimate for the line width for the primary component, based on the measured T2*, is 3.7 Hz.

Figure 12:
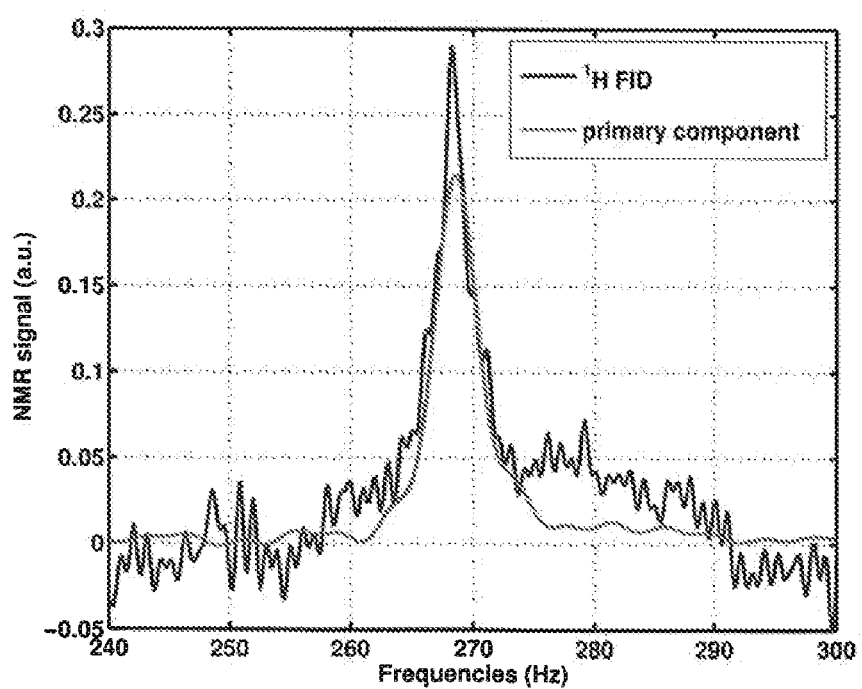
FIG. 12 illustrates a graph where the real part of FID signal for the 1H signal presented in FIG. 11 (blue curve) and the primary component (red curve, resolved by DECRA)

Measurements taken with a water phantom (not shown) indicate the inhomogeneous broadening for the inventors' system is less than 0.5 Hz. Therefore, the inventors believe that the inventors are seeing the natural line width for the subject head matter. FIG. 12 shows the real part of FID signal for the 1H signal presented in FIG. 11 (blue curve) and the primary component (red curve, resolved by DECRA). Such narrow line widths are a key to the work proposed here to measure NMR effects of neuronal currents. The inventors have noted various ways to enhance present capabilities, such as improved cryostat design to reduce the noise level from 8 fT/$\sqrt{Hz}$ down to the noise level of the SQUID, <3 fT/$\sqrt{Hz}$. The use of a SQUID sensor array would also improve signal-to-noise and speed of acquisition. Moreover, the inventors can use higher Bp to increase polarization, although the inventors must limit dB/dt while ramping Bp down to prevent the possibility of peripheral nerve stimulation. The inventors' protocol ramps Bp down from 5 mT to 0 mT in 0.5 msec (dB/dt=10 T/sec). It may also be possible to obtain signals while ramping Bp down more slowly.

The inventors experimentally investigated, using a very simple approach involving magnetomyography (MMG), the possibility of measuring a NMR effect of bioelectric activity. The inventors focused on investigating a change of the total observed decay time of the NMR FID (T2*). The inventors chose to use MMG because of the evidence that the bioelectric currents in muscles are larger than in evoked brain responses. While the cardiac muscle has massive currents, confounding effects such as motion, blood flow, and blood volume of the sample being measured would be extremely difficult to unfold from the data. The inventors collected experimental data for interleaved epochs of NMR recorded while the muscles of the forearm were either stressed or relaxed. This protocol was chosen to try and reduce any hemodynamic or metabolic effects. The SQUID recorded the MMG signal simultaneously with the NMR signal. The MMG signal appears as an increase in white noise which falls off to below the level of the SQUID noise, 20 fT, by 500 Hz. Data NMR were recorded at $\omega L \sim 1$ kHz to minimize any effects on the T2* analysis due to increased noise in the data. The probability density functions (PDFs) for both stressed and relaxed conditions were inferred using a "bootstrap" method. To analyze the data the inventors used the following procedure. Each set of data consisted of approximately 100 relaxed epochs or 100 stressed epochs, extracted from the original collection of randomly presented conditions. For each set, the inventors created a new bootstrapped set of 100 epochs by randomly sampling with replacement from the original set. The 100 epochs were then averaged and a T2* value was initially estimated by DECRA, then the estimate was refined in a nonlinear discrete exponential fit.

Figure 13:
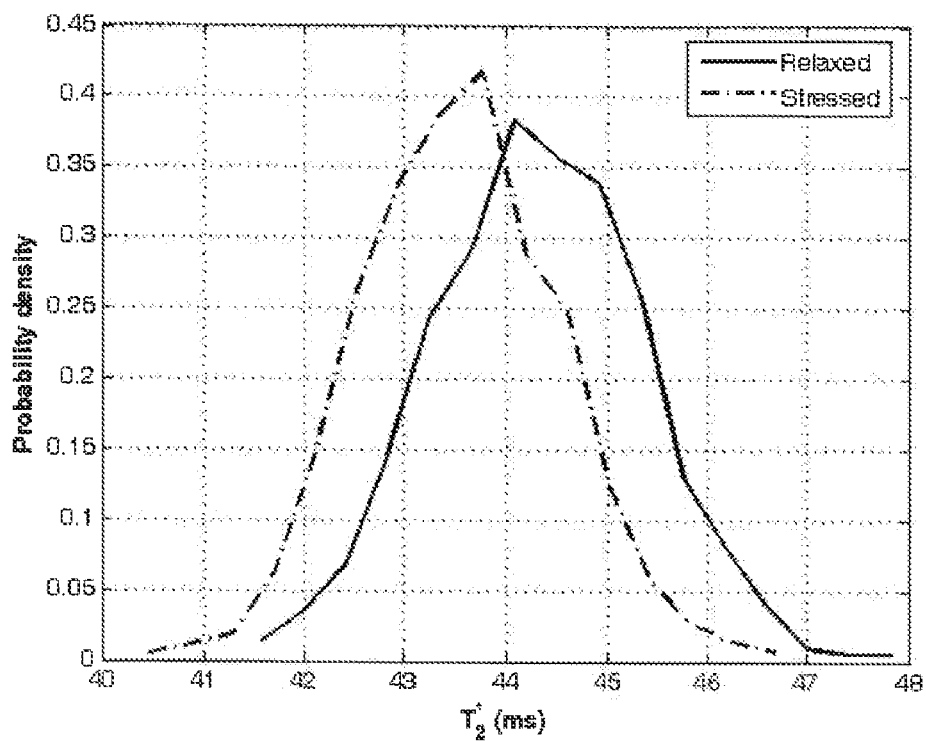
FIG. 13 illustrates a histogram of the T2* and an inferred PDF for each condition from a bootstrap procedure which was repeated 1000 times using different randomly sampled epochs.
Figure 14:
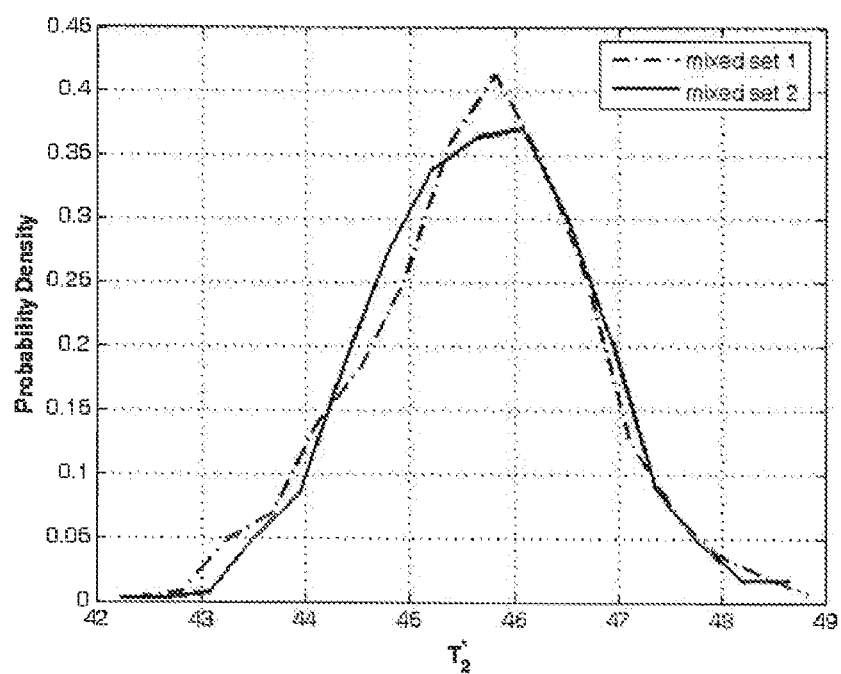
FIG. 14 illustrates a graph wherein permutation randomization was repeated 1000 times, and a histogram of the times was created for each set, to infer the PDF.

This bootstrap procedure was repeated 1000 times using different randomly sampled epochs each iteration. From these bootstrapped trials the inventors created a histogram of the T2* and inferred a PDF for each condition, as shown in FIG. 13. The same analysis approach was then applied to random permutations of the stressed and relaxed sets. The two original sets of 100 trials were pooled into a common set of 200. The pool was then randomly sampled without replacement into two new sets of 100. These two sets were then averaged and the T2* estimate repeated as before for each set. The permutation randomization was repeated 1000 times, and a histogram of the times was created for each set, to infer the PDF shown in FIG. 14. Although the inventors did not have spatial encoding information, they used an experimental set-up with the pre-polarizing coil beneath the subject to maximize the signal from the region where the biomagnetic signals were expected to originate (e.g. a complex set of muscles including the flexor digitorum superficialis, extensor carpi ulnaris, and extensor digiti minimi).

The permutation test (FIG. 14) shows no inherent preference in processing between the two sets, while the bootstrap tests (FIG. 13) suggests that the two conditions may be distinct, but with statistically low power. The observed difference in T2* for the two conditions is not statistically significant; however, it is encouraging that the trend of a shorter T2* for the stressed condition is what one would expect if this effect were due to bioelectric currents dephasing the NMR signal. The data acquired for the other subjects appears to be consistent with these results, although that analysis is still preliminary.

The inventors also caution that even if this effect were statistically significant, they were not yet able to rule out that the measured effect was due to a systematic error due to the slight differences in the experimental configuration between the two cases (i.e. slightly different arm position), some other systematic error in the hardware, or a biological effect that is not electrical in nature. The inventors believe their protocol of interleaved stressed and relaxed epochs eliminates obvious systematic errors due to changes in blood flow, blood volume, or metabolic changes between the stressed and relaxed condition, as these effects would most likely be slower than ~1 s epoch times. The inventors acquired data from three new subjects with a very similar protocol to search for effects of biomagnetic activity in the fore-arm muscles on the spin population. The sets of data displayed significantly better signal-to-noise than the data outlined above. The analysis of the inventors' data indicated multiple components in the FID, which is consistent with reports in the literature of multiple components in the T2 in exercised muscles.

Preliminary analysis of data indicated a more significant and consistent decrease in the T2* times for muscle during exercise as compared to during resting. This is particularly interesting in light of the reports that HF MRI and fMRI measurements of muscles showed that measured T2* times appreciably increased (19% and more) with exercise, contradictory to the patterns observed in the inventors' work. In fact, one report showed an increase in the T2* times after only two repetitions of a contraction exercise. While all of these measurements were made at HF and the T2* times were measured before and 'immediately' after exercise, the hemodynamic effect is clearly in the opposite direction of observed changes lending further strength to the argument that the effect is due to biomagnetic interactions with the NMR spins. Such effects would only be observable during the activity itself and not in the protocols reported.

The inventors have explored the relative contributions of postsynaptic currents (those most responsible for distant fields measured by MEG) and action potential currents (typically ignored in MEG modeling) to the microscopic spatio-temporal field distribution. Their preliminary examination, detailed here, shows that while action potential currents contribute about 1% to the MEG signal, they are responsible for the majority of local magnetic field variations on the Microscopic level. Hence, an operational model necessarily includes both postsynaptic and action potential currents for calculating the microscopic magnetic field distribution.

Figure 15:
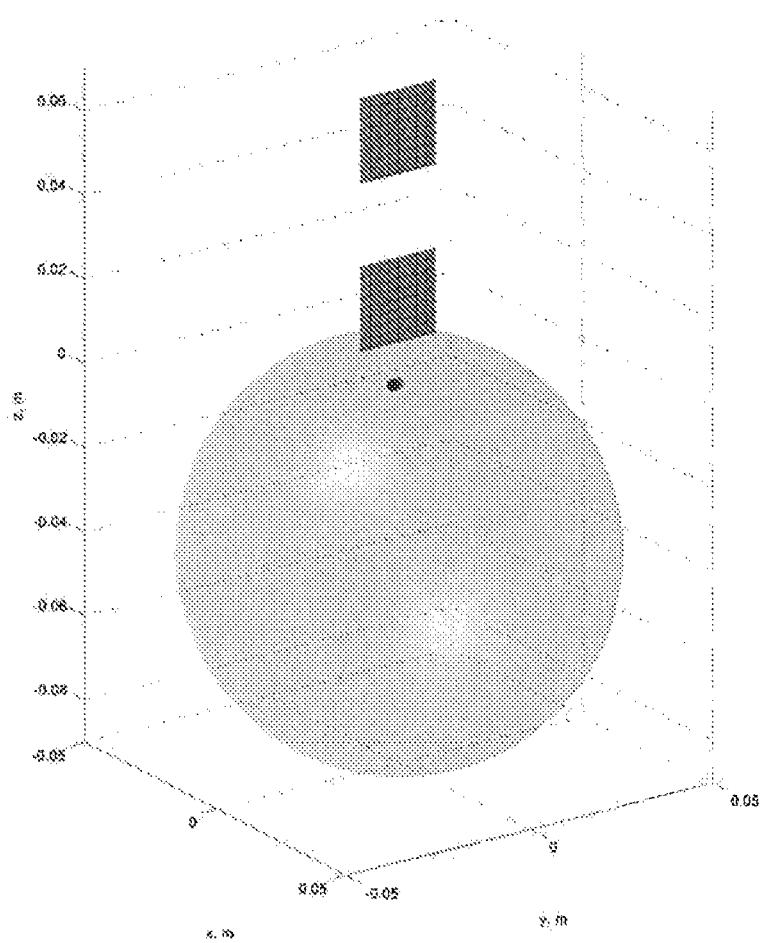
FIG. 15 illustrates the geometry of a model of magnetic fields for a conducting spherical volume of cortical tissue containing a population of 105 neurons randomly placed in a cylinder with diameter of 2 mm and length of 2 mm, where the transparent sphere with the diameter of 100 mm represents conducting volume, the color dots (green, blue, red) represent neurons (less than 1% shown), and the rectangular surfaces represent SQUID pick up coils.

The inventors calculated the magnetic fields for a conducting spherical volume model of cortical tissue containing a population of 105 neurons randomly placed in a cylinder with diameter of 2 mm and length of 2 mm. The geometry of the model is shown in FIG. 15, where the transparent sphere with the diameter of 100 mm represents conducting volume, the color dots (green, blue, red) represent neurons (less then 1% shown), and the rectangular surfaces represent SQUID pick up coils.

While the model is simplistic relative to the inventors best knowledge of cortical tissue, it is far more realistic in its ability to generate the microscopic spatio-temporal magnetic field distribution that one might expect in cortex. Each neuron was modeled as three current dipoles: one dipole with strength of 20 fA-m represents postsynaptic current, and two oppositely oriented dipoles of strength 100 fA-m each separated by 1 mm representing currents associated with an action potential. All dipoles are aligned along y-axis. The fraction of the synchronous population was 50%. The magnetic field calculated at the center of the lower pick-up coil (i.e. 30 mm from the sources) averaged over a large number (>1000) of different configurations of the synchronous population was 226 fT with standard deviation (over the set of different synchronous populations) less then 0.5 ft. The average magnetic field due to currents associated with action potentials was about 3.5 ft. These results are in good agreement with published results obtained with MEG. This result was obtained without adjustment to any model parameters and uses only experimental values for neuronal currents, thus encouraging the inventors that their model was representative of actual cortical structure.

Magnetic fields inside of the volume representing cortex tissue were evaluated at the centers of cells formed by a tetrahedral tessellation of the current dipole locations using a formulae. The average modulus of magnetic field inside was 0.7 nT with standard deviation 0.3 nT over the set of observation points and the set of synchronous populations. The large relative standard deviation reflects both high non-uniformity of magnetic field inside the tissue (as expected) and strong dependence of this field on the configuration of synchronous population. Strong dependence of the magnetic field inside the tissue on the Configuration of the synchronous neuronal population implies that time dependence of that field will have a stochastic character if one assumes random firing of neurons inside that tissue. To evaluate the statistical properties of this process one can assume that the field inside is largely the result of the action potential currents (in the frames of the model used) and the time dependence of the firing of the individual neuron is modeled by a function.

Figure 16:
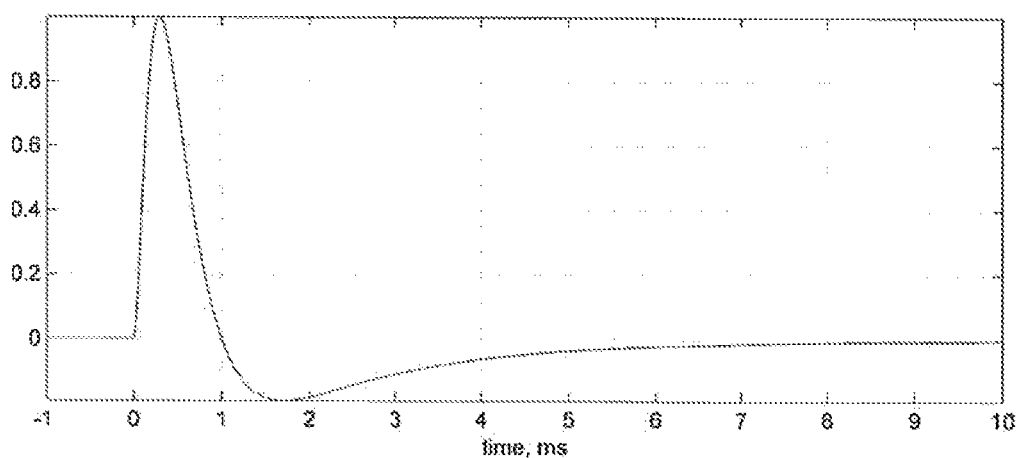
FIG. 16 illustrates time dependence for parameters used in a simulation wherein neurons were randomly activated with a probability that reflected both time dependence of the activation level of the tissue and dead time of an individual neuron.

FIG. 16 illustrates this time dependence for the parameters used in the simulation. The neurons were randomly activated with a probability that reflected both time dependence of the activation level of the tissue and dead time of an individual neuron; the total magnetic field at any given location is the sum of magnetic fields produced by the individual neurons (by superposition).

Figure 17:
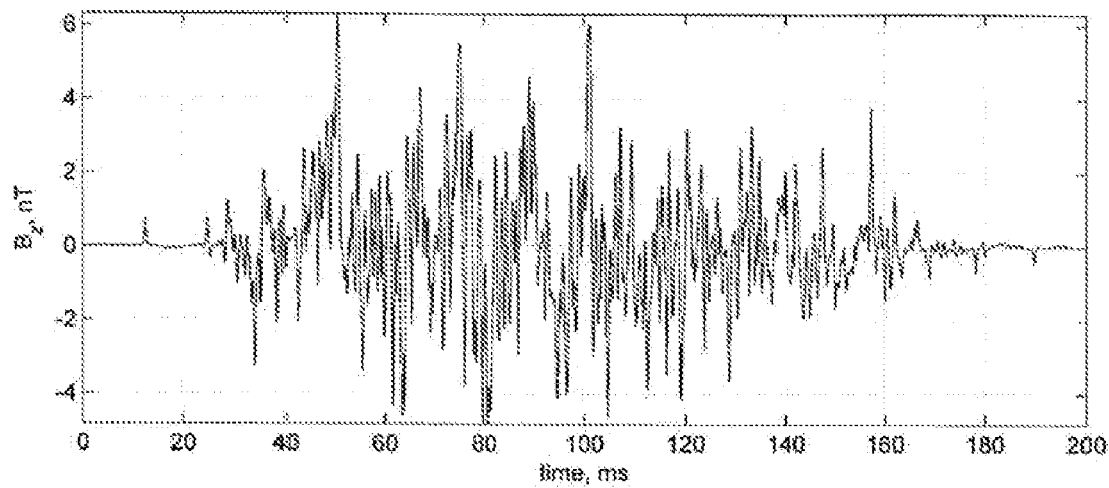
FIG. 17 illustrates a "typical" time course of the z-component of the magnetic field at a "typical" observer location in tissue.
Figure 18:
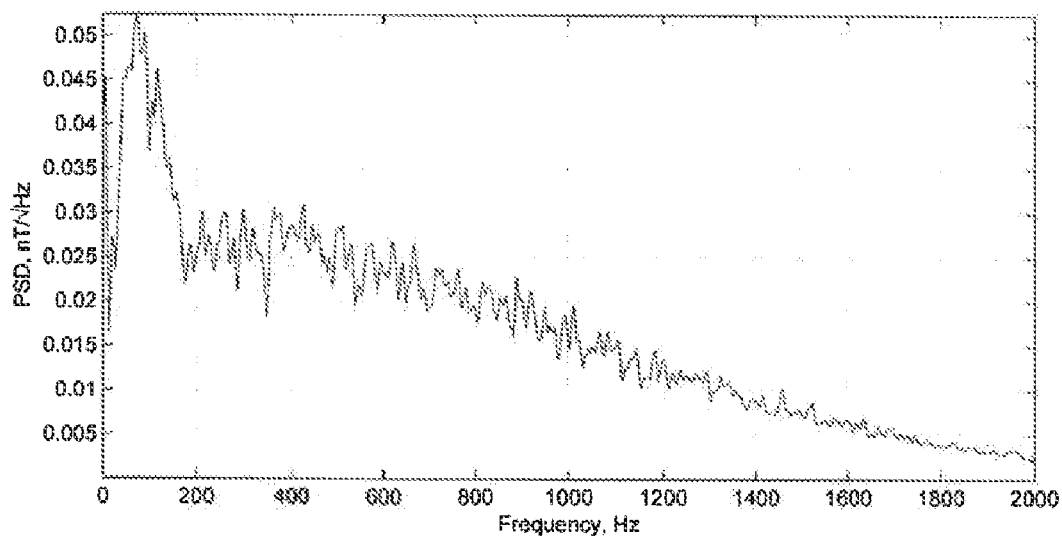
FIG. 18 illustrates the average power spectral density (averaged over a set of observer locations within the tissue) for the magnetic field.

FIG. 17 illustrates a "typical" time course of the z-component of the magnetic field at a "typical" observer location in tissue. The average power spectral density (averaged over a set of observer locations within the tissue) for the magnetic field is illustrated in FIG. 18. These last two figures provide an idea of the temporal character of magnetic fields associated with neuronal activity that can be expected inside cortical tissue. It should be noted, however, that the model is as yet quite simplistic and uses no information about spatio-temporal correlation of neuronal activation, consequently the results obtained thus far should be considered as an illustration of the more complete analysis the inventors sought to accomplish as part of their work.

The effect of randomly oscillatory magnetic fields on the nuclear magnetization can be calculated with a numeric solution of the Bloch equation. The inventors approximated the randomly oscillatory magnetic field at a point inside cortical tissue by a random phase process, $$B_n(t) = B_1 \xi(t) \hat{e}_x, \text{ where } \xi(t) = \int_0^\infty P_{\xi\xi}(\nu) \cos(2\pi\nu + \phi) d\nu$$

where $P_{\xi\xi}(\nu)$ is the one-sided power spectral density, and is uniformly distributed between 0 and. In an example the power spectral density is defined as $$P_{\xi\xi}(\nu) = \begin{cases} 1, & |\nu - \nu_0| < \Delta\nu \\ 0, & |\nu - \nu_0| \geq \Delta\nu \end{cases}$$

Figure 19:
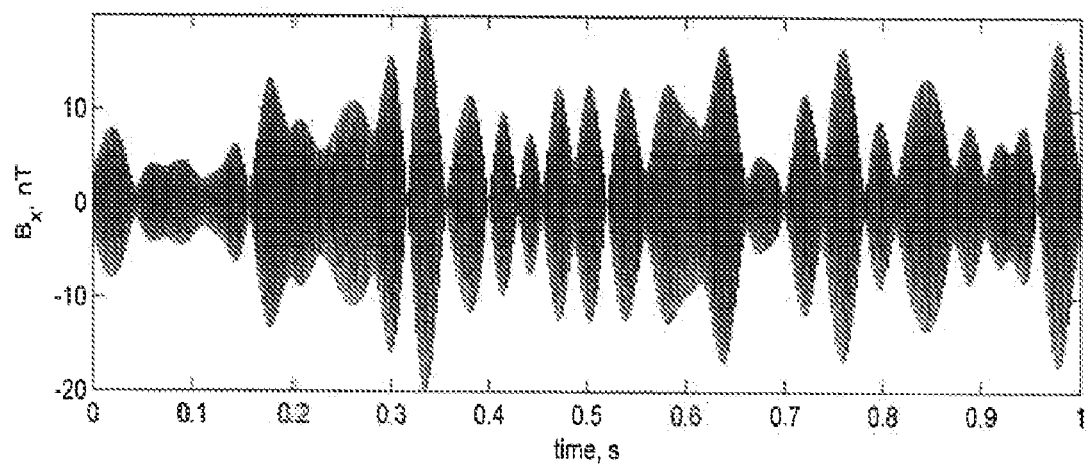
FIG. 19 illustrates a computation of a typical realization of the randomly oscillatory magnetic field.

For a set of sample parameters consistent with ULF measurements, $\nu 0$=425.7713 Hz, B1=1 nT, $\Delta\nu$=20 Hz, the inventors computed a typical realization of the randomly oscillatory magnetic field as shown in FIG. 19.

Figure 20:
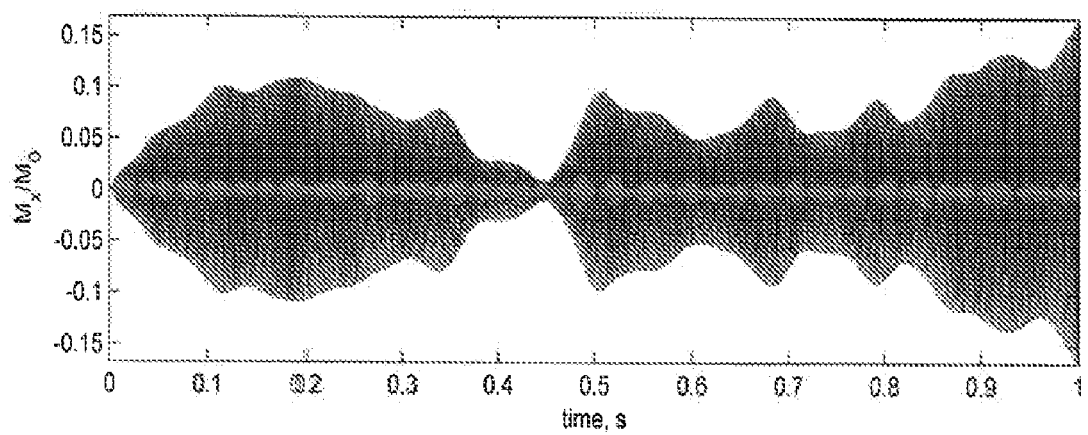
FIG. 20 illustrates the evolution of x-component of nuclear magnetization, Mx, originally aligned along the static magnetic field $B0=B0ez$, for two distinctly different parameter sets.

FIG. 20 illustrates the evolution of x-component of nuclear magnetization, Mx, originally aligned along the static magnetic field B0=B0$e_z$, for two distinctly different parameter sets. Mx represents the magnitude of the NMR signal one would experimentally measure. In the first (red waveform in FIG. 20) the inventors computed the evolution of Mx for the ULF-NMR experiment where $\omega L$ is above the power spectral density envelope (>2000 Hz) of the neuronal activity inside cortical tissue. In the second case (blue waveform in FIG. 20) the inventors computed the evolution of Mx for the ULF-NMR experiment where $\omega L$ is within the power spectral density envelope (~0-1,500 Hz) of the neuronal activity inside cortical tissue. One can clearly see the large amplification of Mx for the case where $\omega L$ is chosen to correspond to the frequency range of neuronal activity. Note that the uppermost frequencies one can expect to observe for neuronal activity is 2,000 Hz which would induce these enhanced interactions with proton spins at no more than 47 µT. Clearly these studies are uniquely limited to ULF-NMR.

While there are significant accomplishments to be realized in the pursuit of direct neuronal imaging, the inventors' results clearly demonstrate the feasibility of the work proposed here. All of the basic technical components from low-noise SQUID measurements of electrophysiological data to magnetic resonance imaging at ULF have been demonstrated. Developed here are the theoretical foundations for building a working (as opposed to a physical) microscopic cellular model that will help tune magnetization protocols to elicit the largest possible signal for DNI.

Figure 21:
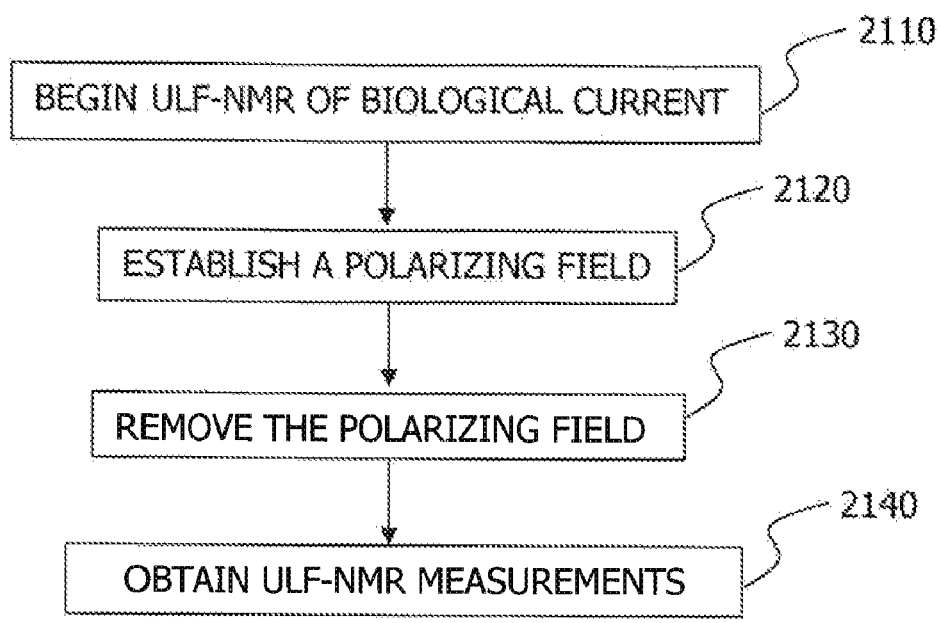
FIG. 21 illustrates a flow diagram of a method of obtaining ULF-NMR measurement of a biological sample in accordance with the present invention.

Reviewing again the method features unique to ULF-NMR biological current measurement, reference is now made to the flow diagram 2100 in FIG. 21. ULF-NMR is begun as shown in step 2110. A polarizing field is established (turned on) as shown in step 2120 in the millitesla regime, in order to generate a significant net polarization in a population. The polarizing field is then removed (turned off) as shown in step 2130 (a step generally impossible at HF due to the power involved). Deactivation of the polarization field as shown in step 2130 allows a measurement field at µT levels aligned perpendicular to the polarizing field to force the population to begin precessing about the measurement field. Measurements are then obtained by ULF-NMR as shown in step 2140.

No "RF" "tipping" pulse is needed to force the population into precession, since the measurement field is already perpendicular to the polarizing field. The precession frequency is dependent on the ULF measurement field, not the stronger polarizing field. Once the precession begins (at either HF or ULF), the general arguments in the literature are that local cellular magnetic fields due to neuronal activity will interact with the free induction decay in a detectable manner. The principal conjecture is that the resulting inhomogeneity of the cellular fields will cause a more rapid dephasing of the FID, i.e. a shorter T2* time.

The inventors' research design follows two general approaches to detecting directly the neuronal currents at ULF. In the first approach, the arguments made in HF-NMR that cellular magnetic fields interact with the FID are effectively extended. ULF-NMR has a unique advantage over HF-NMR, however, in that one can set the measurement magnetic field such that the resulting resonant frequency lies in the power spectrum of neuronal activity. The nuclear precession is now not only affected by the local field inhomogeneity, but it is also greatly affected through resonant absorption of the energy from neuronal activity; such resonant absorption is impossible at HF. Thus dephasing will occur far more rapidly than would simply occur due to local field inhomogeneity, as well as other measurable effects in the FID.

Figure 22:
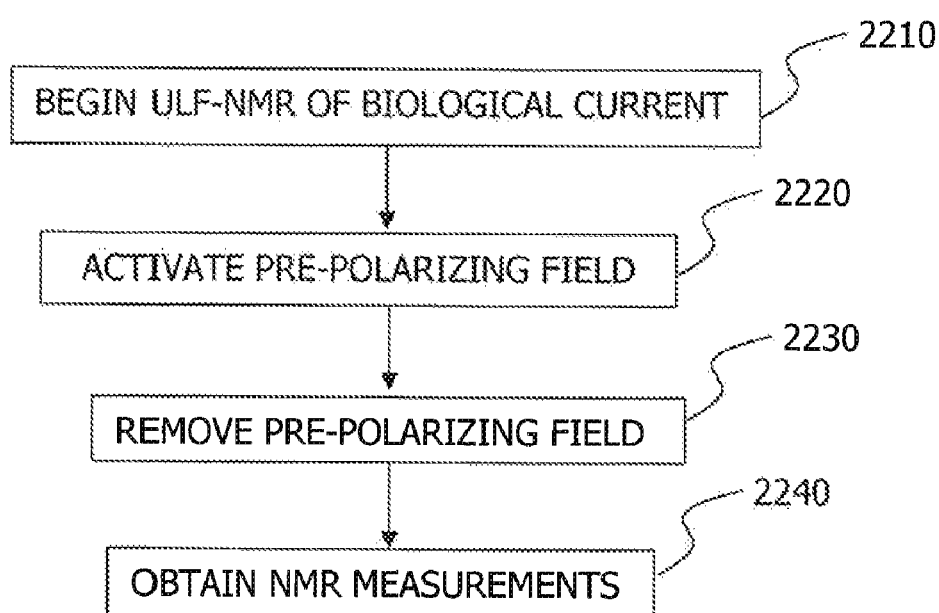
FIG. 22 illustrates a flow diagram of a method of obtaining ULF-NMR measurement of a biological sample in accordance with the present invention.

Another approach unique to ULF-NMR is illustrated in the flow diagram 2200 shown in FIG. 22. Contrary to the first approach, in this approach the pre-polarizing field and the measurement field are now collinear. The ULF-NMR process is begun as shown in step 2210. Next, a pre-polarizing field is activated as shown in step 2220 to establish a net polarization density in the neuronal population. When the pre-polarizing field is removed (switched off) as shown in step 2230, the ultra-low measurement field establishes the Larmor frequency of the population; but since the measurement field is now collinear to the polarizing field, no observable precession will occur in a neutral medium. If, however, neuronal activity is present at the Larmor frequency, the population will absorb this energy with a high-degree of magnification, causing the population spin to "tip" and become observable as a precession. Observable measurement of biological/neural current can be obtained using ULF-NMR as shown in step 2240. In essence, the nuclear magnetic resonance was set up such that the neuronal activity forces the observable precession, rather than applying an external tipping frequency. Again, due to the Larmor frequencies involved at HF (tens of MHz), such resonant absorption of neuronal energy is impossible.

In the sections that follow, the inventors detail their approaches to developing working cellular models, designing test sequences to elicit the desired precession effects, and experimentally testing the inventors' studies in the laboratory.

Developing a Computational Model of Magnetic Fields in Cortical Tissue

Figure 23:
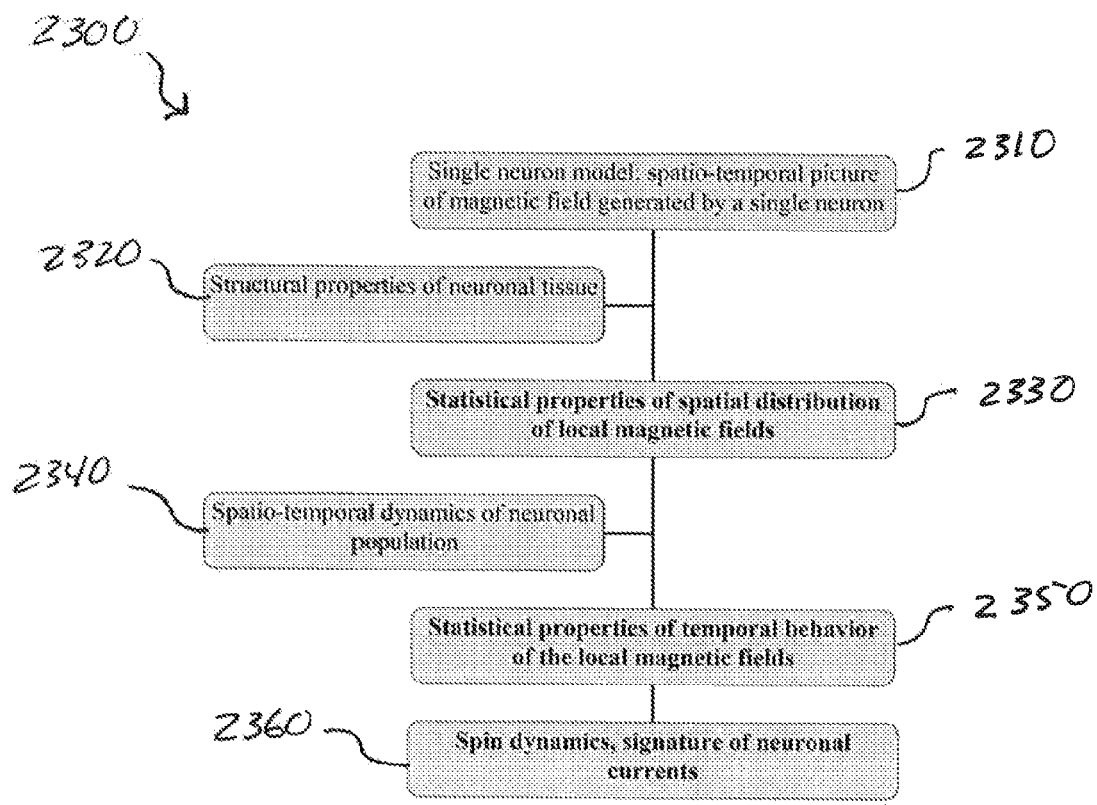
FIG. 23 illustrates a flow diagram of the model development process reflecting incorporation of available information and models used as the inventors built a model on existing knowledge.

In FIG. 23 a chart illustrates the flow diagram 2300 of the model development process reflecting incorporation of available information and models as improved models are built on existing knowledge. The process starts by concentrating on a computational model of a single neuron as shown in block 2310. Using the models developed in the literature, and the inventors' own in-house FEM models, one can infer an accurate picture of the spatio-temporal properties of magnetic fields generated by a single neuron. Using these results (validated against available experimental results, e.g. extracellular potential measurements) as a "gold" standard, one can proceed with development of more computationally efficient models that retain the salient features of the picture allowing rapid prototyping of neuronal density, spacing, and other parameters. One should strive to find an effective balance of computational complexity and physical reality. It should be noted that because one can rely on Monte-Carlo like techniques to infer the aforementioned properties of local magnetic fields, the neuron model should be as computationally efficient as possible.

Using a single-neuron model and the information about structural properties of cortical tissue such as packing density, symmetry, spatial correlation etc. as shown in block 2320, one can study the spatial statistical properties of the magnetic field generated by neuronal currents as shown in block 2330. The approach is to use Monte-Carlo type computational techniques and analytical formalism. The next step incorporates information about the spatio-temporal dynamics of the neuronal population with the model of the magnetic field produced by single neurons and the spatial organization of the neuronal population as shown in block 2340. The spatio-temporal activation behavior of the population is a significant influence on the temporal characteristics of the magnetic field at any point in the tissue.

With the model of the statistical properties of behavior of magnetic fields associated with neuronal currents inside cortical tissue as shown in block 2350, the inventors then modeled their effect on spin dynamics as shown in block 2360. The inventors' approach was to use the numeric solution of Bloch equations, Monte-Carlo techniques, and the quantum mechanical relaxation formalism to infer the statistical properties of dynamics of spins affected by magnetic fields associated with neuronal currents. The experimentally observable NMR signal will be computed from this interaction between the spatio-temporal distribution of neuronal magnetic fields and the nuclear spin population (primarily from water molecules in cortical tissue). Characteristics of the spin population are determined by the externally applied magnetic fields used to polarize the population and the fields about which the spin population precesses. The fields applied by external means to the spin population have traditionally, in HF NMR and MRI, been referred to as the "pulse sequence".

DNI Protocol Design

Beginning with the knowledge gained about perturbation of spins' precession due to neuronal currents obtained from the model described in the previous section, one can investigate various magnetic field protocols at ultra-low fields to determine the best candidates for inducing a measurable NMR signature. The primary approach used to achieve this aim can be to perform "computational experiments" using the highly efficient code constructed to simulate ULF-MRI. This code should be designed and used to calculate NMR signals, and reconstruct images based on magnetic field presentation, specifically designed for ULF. If one assumes the activation of the population of neurons is completely random (i.e. no spatial correlation between neurons of the synchronous population), then the most observable effect will likely be the change of the observed relaxation time T1 due to neuronal activity. Certainly, this hypothesis requires further investigation.

If one assumes that the activation of a synchronous population of neurons has spatial correlation of the order of a millimeter, then one would expect changes both of T1 and T2 relaxation times and likely a change in the local phase. A first method follows conventional arguments currently being pursued by high field MRI researchers. One can study various approaches for the T1-weighted and T2-weighted MRI at ULF, optimizing parameters of the field protocols to maximize the expected effects of neuronal currents. An example of such a field protocol would be 1) application of a strong pre-polarizing field to a sample, followed by an ultra-low "relaxation" field that will enable investigation of changes in T1 and/or T2 relaxation times (depending on orientation of the "relaxation" field) as a function of neuronal activation. Neuronal activation is controlled by the current applied (in the case of phantom studies), or the presentation of stimuli (in the case of human studies). For this protocol (and most others) one can optimize magnitude, orientation (both relative to the polarization field and relative to the alignment direction of the neuronal population) and duration of the "relaxation" field. Performing these studies at ULF provides the unique capability to easily control the orientation and magnitude of polarization, relaxation, and measurement fields.

The second method that can be pursued is based on the resonant absorption of energy from the neuronal magnetic fields by the spin population. This effect is unique to ULF MRI. As in the previous method, established is a net polarization density in the cortical tissue by applying a strong polarization field, together with a much weaker 'measurement field'. When this prepolarizing field is switched off, the remaining ultra-low measurement field collinear to the net magnetization establishes the Larmor frequency of the population, but since the measurement field is collinear to the pre-polarizing field, no observable precession signal will occur in a neutral medium. If, however, neuronal activity is present at the Larmor frequency, the magnetic field associated with this activity will cause "tipping" of the net magnetization resulting in observable precession. In essence, the nuclear spin population is predisposed such that the neuronal activity forces the observable precession, rather than applying an external tipping field. It should be noted that for small angle tilting of the net magnetization the changes in transverse component of the magnetization are much larger then changes of the longitudinal component, thus detecting transverse components in such a configuration could in principle be a very sensitive method of detecting neuronal activity. Again, only because of the overlap between the frequencies of neuronal activity and the Larmor frequencies at ULF is such an effect possible.

Experimental Validation of the DNI signal

Further described herein is a selection of relatively simple experiments to demonstrate the detection of the NMR signal that results from the interaction between neuronal activity and the spin population. Phantom experiments will focus on the effect of temporal dynamics of the neuronal currents on the NMR signal, because it will be far beyond the scope of this effort to construct a phantom representative of the spatial characteristics of cortical tissue. One should rely on experiments with human subjects to best demonstrate the NMR signature resulting form the interaction of neuronal currents in cortex with the spin population. The present inventors have already designed, built, and tested the experimental equipment and expertise necessary to present stimuli, manipulate magnetic fields, and measure NMR signatures. The equipment can be quite similar to that pictured in FIG. 10. The system can include of a cryostat containing a single channel planar gradiometer coupled to a SQUID sensor placed directly adjacent to the visual cortex. The system should demonstrate the unambiguous measurement of a NMR signature of the spin population interacting directly with neuronal currents.

Simple Wire and Anthropomorphic Phantoms

One can use two types of phantoms in experimental studies, a simple wire phantom in water and a more complex anthropomorphic phantom available to this project. As contrasted to the human condition, the FID of water is simple, well-understood, and most importantly very long and stable, such that one can more easily detect interactions of the phantom currents with the FID in the early stages of validation. To simulate a more human-like condition and bounded shape, an unusual phantom was utilized as illustrated in the photograph of FIG. 21. A natural bone human skull is covered by layers of conducting latex to simulate a scalp necessary in EEG recordings. The interior of the skull comprises optically-isolated current dipole sources, each 0.2 mm in diameter, that can be bent into relatively arbitrary configurations. After initial insertion of the sources through the base, the interior of the skull is filled with a hot conducting gelatin that also perfuses the natural bone layers, providing a reasonable facsimile to the true diploic spaces filled with liquors inside the living human skull. The sources are MEG compatible, making simultaneous EEG and MEG recordings possible under otherwise highly controlled experimental conditions.

The inventors have experimentally measured the FID of the gelatin and confirmed that it is in the 100 s of milliseconds and therefore suitable for testing for interactions with local current fields. It should be noted that such a phantom can only test macroscopic effects of dipolar sources on the FID, not the cellular-level interactions proposed in the models. Nonetheless, such a phantom will help demonstrate some of the basic dephasing of FIDs driven by local field inhomogeneities resulting from current flow.

Since the phantom is both EEG and MEG compatible, it can also serve to demonstrate simultaneous measurements of direct current imaging and virtual E/MEG. The initial focus by the inventors was on a single dipole isolated in the medium adjacent the parietal regions, as a surrogate to the proposed visual studies (described in the next section below). In both phantoms, the experimental sources enabled the simulation experimentally of the overall temporal dynamics of source activity. One can generate a single pulse temporal sequence through the source, such as was shown in FIG. 16 in Section C above, to study its effects on NMR, as a rough approximation of the fields inside cortical tissue. More interestingly, generated can be the time sequence such as was shown in FIG. 17 that is more representative of a tissue region.

For a given model of cortical tissue, a small number of experimental cortical dipoles can be placed in close proximity and given composite time series, such that at a distance the net appearance of the dipoles mimics that of the tissue. Since the inventors' sources were optically isolated, one can lash together several in a relatively small region and drive them separately. The power spectral density of this sequence in this cluster enabled a more direct experimental test of the resonant absorption effects both in and out of band, such as was modeled in FIG. 20.

Using these phantoms, one can experimentally confirm the inventors' polarization and measurement sequences to ensure initially that the theoretical sequences are indeed experimentally generated. Manipulating the parameters in the inventors' protocol design, one can then test that detectable changes in the FID occur. The key feature of the FID to be examined is the change in decay time, expressed as the observed exponential decay parameter $T2^*$.

One can subject sets of the data generated under both quiescent and activated conditions to bootstrap analyses to demonstrate that observable differences between the two conditions are stable and significant. Other key parameters to test are changes in the amplitude, frequency, or phase of the FID. The set of parameters (as opposed to individual) will also be subjected to standard pattern classification analyses to further delineate the discrimination between sets. Of course, such phantom experiments are only a very rough approximation to the exquisite cellular structure present in cortical tissue. Nonetheless, these experimental validations with simple dipolar sources will help bridge the model cellular theory with the experimental human condition, discussed next.

Human Subject Studies

The anthropomorphic or simpler phantoms will be used to confirm some of the basic dephasing and resonant absorption concepts in models discussed herein at the macroscopic levels. While these validation steps are important to understanding the biophysics of the model, the only real validation of the model and ultimately the proposed technique is to measure the effect in the living human brain. The complexity of cortical structure and neuronal activation is far beyond the capabilities of any reasonable physical phantom to simulate. It can be appreciated that the ultimate test subject is the human brain.

An important function of the single cell compartmental model described herein is to enable testing protocols, particularly in the way that magnetic fields are applied to the sample or subject, to maximize the NMR signal indicative of neuronal activation. Normal control subjects can be subjected to stimuli using evoked response protocols that have been demonstrated to elicit significant activation of cortical tissue. The ability to measure the effect of neuronal activity on the NMR signal using the system and methods described herein is achievable provided a neuronal activation that can be deterministically event-related involving significant volumes of cortex. Event-related (or evoked) responses enable researchers to interleave epochs of NMR pulse sequences with stimuli and epochs without stimuli. Test subjects should have periods of presentation of an alternating or flashing checkerboard pattern interleaved with periods of a neutral gray or dark screen, in order to establish relatively quiescent periods of visual activity relative to periods with a large region of the cortex activated. The acquired data provide the basis for comparison of the two sets of NMR epochs and statistical analyses as described above. Bootstrapping analyses can be applied to measured data. As in the muscle data presented above, the FIDs from both periods can then be evaluated for significant differences in dephasing time, amplitude variations, or frequency shifts. The data sets can also be randomly permuted to test for systematic effects and natural random variation.

One can rely initially on the bootstrap technique to test for stability and significance of the measurements. Observations of apparent noise levels in the data can then be fed back into the models for confirmation by Monte Carlo methods in simulations. Once can use visual stimuli because of the large-area activation, measure of control given by the style of presentation, and reported activation of specific frequencies in brain activity induced by these stimuli. For example, visual stimuli such as a reversing large-area checkerboard pattern or a flashed large-area checkerboard pattern have been shown to involve reproducible large-area activations with good subject-to-subject consistency in the areas of activation. Correlations between the extent of activation (as determined by the number of BOLD activated voxels) and pattern luminance intensity contrast have also been reported. By using large-area reversing or flashed checkerboard patterns, large-scale activation of the visual cortex can be assured, and the size, placement, and luminance intensity will enable the measurement of control of the areas and extent of activation in visual cortex. It should be noted that, while significant alpha activation can be realized by a subject simply closing their eyes, the timing would be far more difficult to control.

It has been found that periodic presentation of a checkerboard pattern will elicit a strong, entrained response at the driving frequency. Indeed, they reported the power spectral density of neuronal activity (measured by MEG) in the frequency band around the presentation frequency increased by almost an order of magnitude. While it is not immediately clear how the MEG-measured spectral density of brain activity will map to the frequency content of the magnetic fields at the cellular scale, it is plausible to argue that periodic presentation of the visual stimulus will enhance a frequency band of the magnetic fields at the microscopic scale. Hence, by scanning the NMR measurement field, $B_m$, over a magnetic field range (equivalent to saying one should scan over a range of $\omega L$) one can search for fields (and $\omega L$) at which an enhanced DNI effect (NMR relaxation) is observed. Such an enhanced DNI effect would be indicative of an enhanced spectral density of neuronal activity at the cellular level, due to the resonant absorption effect described in this proposal. The prospect of being able to noninvasively measure the spectral density of neuronal activity on the microscopic scale is an exciting prospect, and an observation one may be able to demonstrate in this proposed work.

The reader may note that the magnetic field required to search for resonant absorption effects at tens or even hundreds of Hz are in the 1-10 T range. These fields are substantially below the Earth's magnetic field, commonly 40-50 T. Consequently, these measurements must be performed inside a magnetically shielded room (MSR) or using field compensation coils.

The feasibility of using the well known quantum effect of resonant interactions to directly and tomographically image neural activity in the human brain using magnetic resonance imaging (MRI) techniques at ultra-low field (ULF) has been described. In addition, an approach has been established that is sensitive to magnetic field distributions local to the spin population in cortex at the Larmor frequency of the measurement field. Because the Larmor frequency can be readily manipulated (through varying $B_m$), one can also envision using ULF-DNI to image the frequency distribution of the local fields in cortex. Such information, taken together with simultaneous acquisition of MEG and ULF-NMR signals, would enable the exciting prospect of noninvasively exploring the correlation between local fields induced by neural activity in cortex and more 'distant' measures of brain activity such as MEG and EEG.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those skilled in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The embodiments of the invention in which an exclusive property or right is claimed are defined as follows. Having thus described the invention what is claimed is:

1. A method for obtaining biological current measurements of a sample population comprising the steps of:
   establishing a polarizing field in the presence of a sample population, said polarizing field generating a significant net polarization in the sample population;
   removing the polarizing field from the sample population thereby enabling a measurement field at µT levels aligned perpendicular to the polarizing field to force the sample population to begin precessing about the measurement field; and
   obtaining ULF-NMR measurements of the sample population.

2. The method of claim 1 wherein the sample population is neuronal.

3. The method of claim 1 wherein the sample population is a human brain.

4. The method of claim 2 wherein the sample population is a human brain.

5. A method of obtaining biological current measurements of a biological sample using ULF-NMR, comprising the steps of: establishing a pre-polarizing field and an ultra-low measurement field collinear with each other before a sample, wherein the pre-polarizing field is activated to establish a net polarization density in the biological sample; removing the pre-polarizing field enabling the ultra-low measurement field to establish a Larmor frequency of the biological sample, wherein no observable precession occurs in a neutral medium because the ultra-low measurement field is collinear to the polarizing field unless neuronal activity is present at the Larmor frequency where after the biological sample absorbs the energy causing the biological sample to become observable as a precession; and obtaining observable measurements of biological current using ULF-NMR.

6. The method of claim 5 wherein the biological sample is a neuronal population.

7. The method of claim 5 wherein the biological sample is a human brain.

8. A system for obtaining biological current measurements from a biological sample using ULF-NMR, comprising: a cryostat; a pre-polarization module located in the cryostat; and a detector located in the cryostat.

9. The system of claim 8 wherein said pre-polarization module includes wire-round coils adapted to generate a pre-polarizing field from 4-30 mT.

10. The system of claim 8 wherein said detector further comprises at least one SQUID sensor adapted for measurement fields of 2-25 µT.

11. The system of claim 8 wherein said pre-polarization module includes wire-round coils adapted to generate a pre-polarizing field from 4-30 mT; and said detector further comprises at least one SQUID sensor adapted for measurement fields of 2-25 µT.

12. The system of claim 8 wherein said cryostat is adapted such that biological samples are located outside of the cryostat at room temperature during measurement by the system.

13. The system of claim 10 wherein said SQUID sensor associated with said detector further comprises a low-Tc SQUID coupled to a superconducting second-order axial gradiometer.

14. The system of claim 11 wherein said SQUID sensor associated with said detector further comprises a low-Tc SQUID coupled to a superconducting second-order axial gradiometer.

15. The system of claim 8 wherein said cryostat is a fibreglass liquid helium cryostat.

16. The system of claim 8 wherein said cryrostat includes a tail end facing a sample and said pre-polarization module is adapted to provide a pre-polarizing field (Bp) and includes two wire-round coils positioned around the tail end of the cryostat, coaxial to a gradiometer.

17. The system of claim 16, wherein said two wire-round coils include 250-turns each, are 80 mm in diameter and are separated by 60 mm.

18. The system of claim 8 wherein said detector further comprises a square Helmholtz coil adapted to provide a measurement field, Bm, orthogonal to said Bp.

19. The system of claim 18 wherein said square Helmholtz coil is 56 cm long.

20. The system of claim 8 wherein said cryrostat includes a tail end facing a sample and said pre-polarization module is adapted to provide a pre-polarizing field (Bp) and includes two wire-round coils positioned around the tail end of the cryostat, coaxial to a gradiometer, and said detector further comprises a square Helmholtz coil adapted to provide a measurement field, Bm, orthogonal to said Bp.

* * * * *